(12) United States Patent
Ku et al.

(10) Patent No.: US 12,161,401 B2
(45) Date of Patent: Dec. 10, 2024

(54) DEVICES, SYSTEMS, AND METHODS FOR MONITORING AND/OR CONTROLLING DEPLOYMENT OF A NEUROMODULATION ELEMENT WITHIN A BODY LUMEN AND RELATED TECHNOLOGY

(71) Applicant: Medtronic Ireland Manufacturing Unlimited Company, Dublin (IE)

(72) Inventors: Vincent Ku, Palo Alto, CA (US); Sowmya Ballakur, Ithaca, NY (US); Jignesh Shah, San Jose, CA (US)

(73) Assignee: Medtronic Ireland Manufacturing Unlimited Company, Dublin (IE)

( * ) Notice: Subject to any disclaimer, the term of this patent is extended or adjusted under 35 U.S.C. 154(b) by 0 days.

(21) Appl. No.: 18/521,922

(22) Filed: Nov. 28, 2023

(65) Prior Publication Data
US 2024/0090945 A1 Mar. 21, 2024

Related U.S. Application Data

(63) Continuation of application No. 16/802,408, filed on Feb. 26, 2020, now Pat. No. 11,857,249, which is a
(Continued)

(51) Int. Cl.
*A61B 18/14* (2006.01)
*A61N 1/36* (2006.01)
(Continued)

(52) U.S. Cl.
CPC ...... *A61B 18/1492* (2013.01); *A61N 1/36057* (2013.01); *A61N 1/36139* (2013.01); *A61B 2018/00267* (2013.01); *A61B 2018/00404* (2013.01); *A61B 2018/00434* (2013.01); *A61B 2018/00511* (2013.01); *A61B 2018/00577* (2013.01); *A61B 2018/00875* (2013.01); *A61B 2018/00898* (2013.01);
(Continued)

(58) Field of Classification Search
CPC ...... A61B 18/1492; A61B 2018/00267; A61B 2018/00404; A61B 2018/00434; A61B 2018/00511; A61B 2018/00577; A61B 2018/00875; A61B 2018/00898; A61B 2018/144; A61B 2018/1475; A61N 1/0551; A61N 1/36057; A61N 1/36139
See application file for complete search history.

(56) References Cited

U.S. PATENT DOCUMENTS

| | | | |
|---|---|---|---|
| 2004/0172111 A1* | 9/2004 | Hijii | A61B 5/0538 607/101 |
| 2012/0004656 A1* | 1/2012 | Jackson | A61B 18/1485 606/41 |

\* cited by examiner

*Primary Examiner* — Tigist S Demie
(74) *Attorney, Agent, or Firm* — Shumaker & Sieffert, P.A.

(57) ABSTRACT

The present disclosure relates to devices, systems and methods providing evaluation and feedback to an operator of a device providing neuromodulation treatment, such as modulation of renal nerves of a human patient. In one embodiment, for example, a system monitors parameters or values generated before treatment. Feedback provided to an operator is based on the monitored values and relates to an assessment of various electrical properties associated with an electrode carried by a catheter. The electrode measures an electrical property of biological material making contact with the electrode while deploying the electrode, the electrical property being dependent on a ratio of a wall-interface area to a fluid-interface area.

20 Claims, 12 Drawing Sheets

Related U.S. Application Data continuation of application No. 14/696,058, filed on Apr. 24, 2015, now Pat. No. 10,610,292.

(60) Provisional application No. 61/984,533, filed on Apr. 25, 2014, provisional application No. 61/984,170, filed on Apr. 25, 2014.

(51) Int. Cl.
*A61B 18/00* (2006.01)
*A61N 1/05* (2006.01)

(52) U.S. Cl.
CPC . *A61B 2018/144* (2013.01); *A61B 2018/1475* (2013.01); *A61N 1/0551* (2013.01)

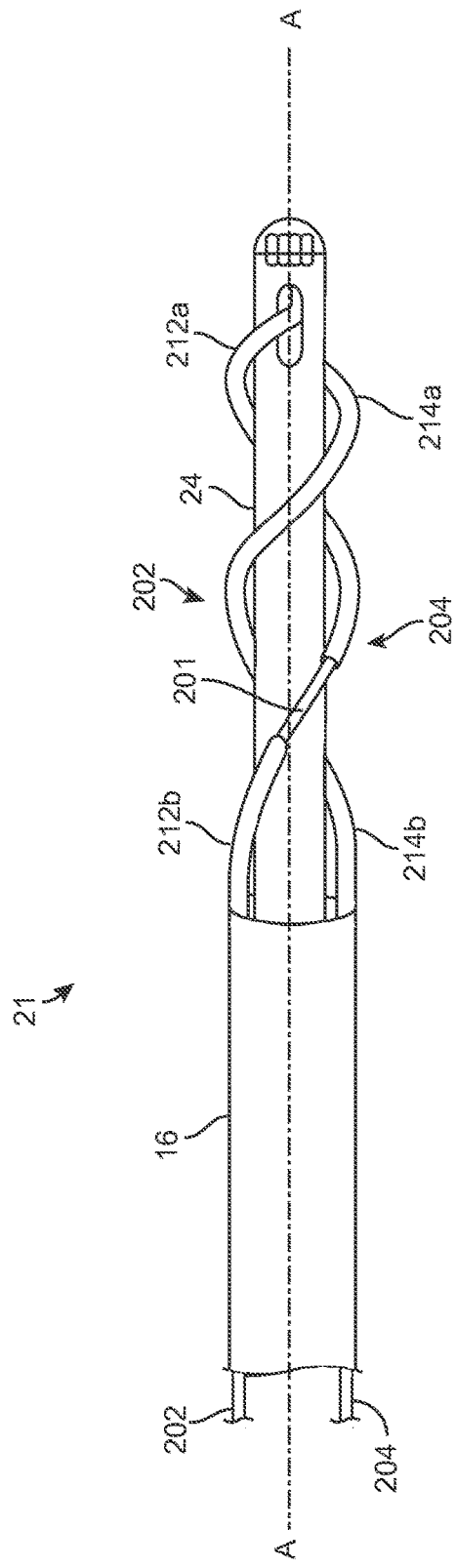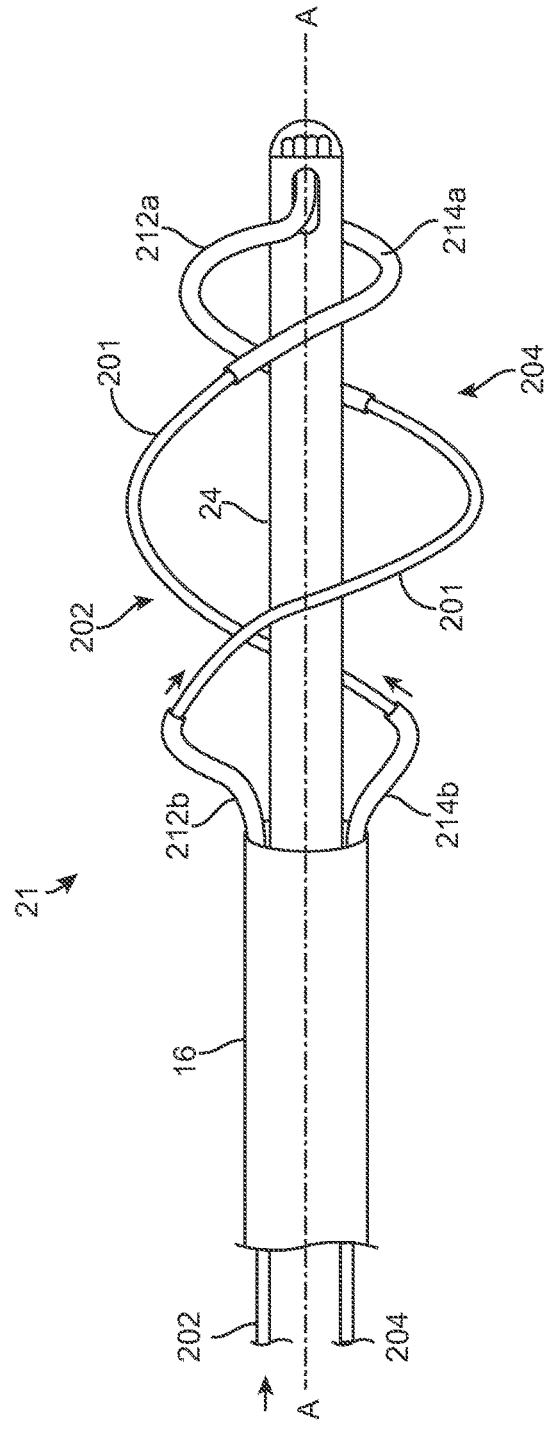
FIG. 2A
FIG. 2B

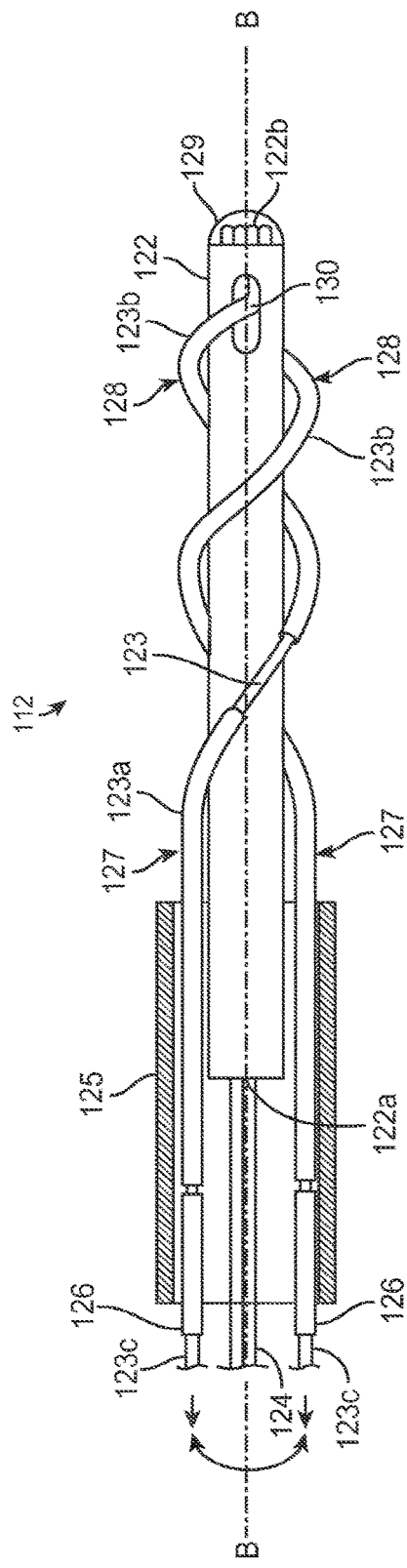
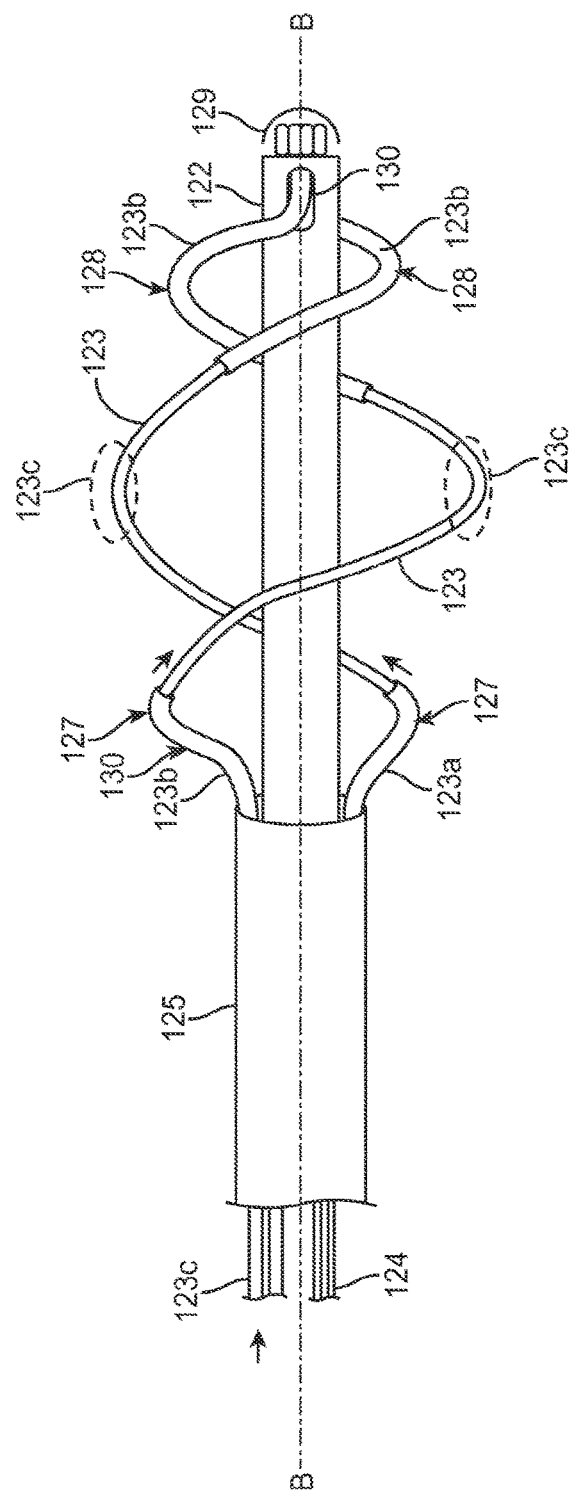

DEVICES, SYSTEMS, AND METHODS FOR MONITORING AND/OR CONTROLLING DEPLOYMENT OF A NEUROMODULATION ELEMENT WITHIN A BODY LUMEN AND RELATED TECHNOLOGY

CROSS-REFERENCE TO RELATED APPLICATION(S)

This application is a continuation of U.S. patent application Ser. No. 16/802,408, filed Feb. 26, 2020, which is a continuation of U.S. patent application Ser. No. 14/696,058, filed Apr. 24, 2015 and issued on Apr. 7, 2020 as U.S. Pat. No. 10,610,292, which claims the benefit of U.S. Provisional Patent Application No. 61/984,533, filed on Apr. 25, 2014 and U.S. Provisional Patent Application No. 61/984,170, filed on Apr. 25, 2014, the disclosures of each of these applications being incorporated by reference herein in their entirety.

TECHNICAL FIELD

The present disclosure relates to neuromodulation and, more particularly, to devices, systems, and methods for monitoring and/or controlling deployment of a neuromodulation element within a body lumen and related technology.

BACKGROUND

The sympathetic nervous system (SNS) is a primarily involuntary bodily control system typically associated with stress responses. SNS fibers that innervate tissue are present in almost every organ system of the human body and can affect characteristics such as pupil diameter, gut motility, and urinary output. Such regulation can have adaptive utility in maintaining homeostasis or preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. For example, radiotracer dilution has demonstrated increased renal norepinephrine ("NE") spillover rates in patients with essential hypertension.

Cardio-renal sympathetic nerve hyperactivity can be particularly pronounced in patients with heart failure. For example, an exaggerated NE overflow from the heart and kidneys is often found in these patients. Heightened SNS activation commonly characterizes both chronic and end stage renal disease. In patients with end stage renal disease, NE plasma levels above the median have been demonstrated to be predictive of cardiovascular diseases and several causes of death. This is also true for patients suffering from diabetic or contrast nephropathy. Evidence suggests that sensory afferent signals originating from diseased kidneys are major contributors to initiating and sustaining elevated central sympathetic outflow.

Sympathetic nerves innervating the kidneys terminate in the blood vessels, the juxtaglomerular apparatus, and the renal tubules. Stimulation of the renal sympathetic nerves can cause increased renin release, increased sodium (Na+) reabsorption, and a reduction of renal blood flow. These neural regulation components of renal function are considerably stimulated in disease states characterized by heightened sympathetic tone and likely contribute to increased blood pressure in hypertensive patients. The reduction of renal blood flow and glomerular filtration rate that result from renal sympathetic efferent stimulation are likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

As shown in FIG. 1, the catheter can include a neuromodulation element.

FIG. 2A is a side view of the neuromodulation element of FIG. 1 in a low-profile delivery state.

FIG. 2B is a side view of the neuromodulation element of FIG. 1 in an expanded treatment state.

FIG. 5C is a profile view illustrating a neuromodulation element in a delivery state.

FIG. 5D is a profile view illustrating the neuromodulation element shown in FIG. 5C in a deployed state.

DETAILED DESCRIPTION

Figure 1:
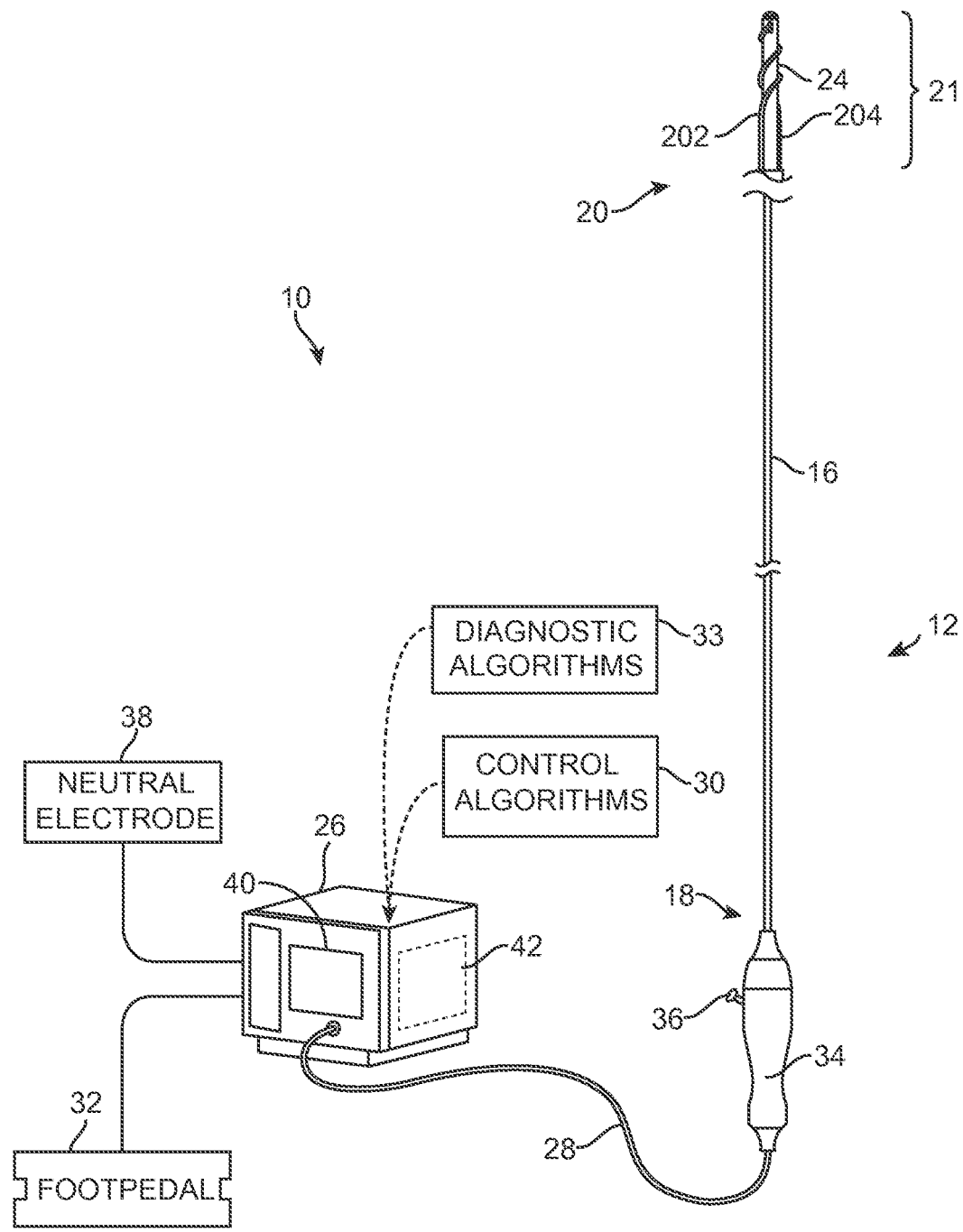
FIG. 1 is a partially-schematic perspective view illustrating a neuromodulation system including a catheter configured in accordance with an embodiment of the present technology.

The present technology is generally directed to devices, systems, and methods for monitoring and/or controlling deployment of a neuromodulation element within a body lumen and related technology. Among other contexts, the present technology can be useful in the context of electrically- and/or thermally-induced renal neuromodulation, which is described in detail below. In at least some embodiments, one or more pre-neuromodulation parameters are measured and analyzed to evaluate electrode contact, to customize power delivery via an electrode, and/or for another suitable purpose. Impedance through an electrical circuit at a treatment site is one example of a potentially useful parameter. Impedance or another suitable monitored parameter can be analyzed based on defined criteria. Based on this analysis, one or more aspects of a neuromodulation treatment may be controlled, customized, or otherwise modified to enhance the treatment.

Methods in accordance with at least some embodiments of the present technology allow for enhanced verification of adequate deployment of a neuromodulation element at a treatment site (e.g., adequate contact between an electrode of a neuromodulation element and tissue at a treatment site) prior to initiating energy delivery. This can be a significant advantage over conventional counterparts. For example, with at least some conventional neuromodulation systems, inadequate deployment of a neuromodulation element can only be detected after energy delivery has been initiated, such as by recognizing a less than expected increase in temperature at a treatment site. This approach is suboptimal at least because it can be difficult to account for partial treatment, if any, that occurred before inadequate deployment of a neuromodulation element is recognized.

Methods in accordance with at least some embodiments of the present technology include using impedance for the purpose of detecting inadequate deployment of a neuromodulation element. In a particular embodiment, a method includes advancing a catheter including an elongate shaft and a neuromodulation element operably connected to the shaft toward a treatment location within a body lumen of a human patient. The neuromodulation element can include an elongate electrode slidably disposed within a dielectric sleeve. After advancing the catheter, the neuromodulation element can be deployed at the treatment location. In one embodiment, deployment of the neuromodulation element can include a first deployment phase during which an electrode of the neuromodulation element moves radially outward while a first interface area between the electrode and the dielectric sleeve decreases and a second interface area between the electrode and a biological fluid (e.g. blood) at the treatment location increases. The first deployment phase can be followed by a second deployment phase during which the first interface decreases and a third interface area between the electrode and a lumen wall at the treatment location increases. The second deployment phase can be followed by a third deployment phase during which the electrode moves radially outward and the third interface area is more stable than it is during the second deployment phase. While deploying the neuromodulation element, the electrode can measure an electrical property of a sum of material adjacent to the electrode. The sum of material adjacent to the electrode can include portions of the dielectric sleeve, the lumen wall and the biological fluid adjacent to the electrode. The method can further include detecting a transition of the electrical property corresponding to a transition from the first deployment phase to the second deployment phase and generating a status indication, enabling a neuromodulation treatment, or both in response to detecting the transition of the electrical property.

As an additional or alternative advantage, methods in accordance with at least some embodiments of the present technology allow a transverse cross-sectional dimension (e.g., diameter) at a treatment site to be determined prior to initiating energy delivery. This can be useful to allow subsequent energy delivery to be customized according to the determined dimension. For example, a treatment carried out in a small blood vessel may call for less energy to be delivered relative to a treatment carried out in a larger blood vessel. In a particular embodiment, methods include advancing a catheter including an elongate shaft and a neuromodulation element operably connected to the shaft toward a treatment location within a body lumen of a human patient. The neuromodulation element can include an elongate electrode slidably disposed within a dielectric sleeve. The elongate control member can be moved relative to the shaft and/or the shaft can be moved relative to the control member so as to cause a longitudinal shift between the control member and the shaft. The longitudinal shift can cause the electrode to move radially outward while a wall-interface area between the electrode and a lumen wall at the treatment location increases. While moving the control member, the longitudinal shift can be measured. While the electrode moves radially outward, an electrical property of a sum of material adjacent to the electrode can be measured. The sum of material adjacent to the electrode can include portions of the dielectric sleeve, the lumen wall and the biological fluid adjacent to the electrode. The method can further include detecting a transition of the electrical property corresponding to a stabilization of the wall-interface area. E.g., physical stability of the electrode with respect to the lumen wall causes the size of the wall-interface area to become constant or nearly so, as detected by the measured electrical property. Energy may be delivered to one or more nerves of the patient via the electrode according to a profile of energy over time. The profile of energy can be based on the longitudinal shift at the time of the transition of the electrical property, and the longitudinal shift at the time of the transition of the electrical property can correspond to a diameter of the body lumen.

Specific details of several embodiments of the present technology are described herein with reference to FIGS. 1-10. Although many of the embodiments are described herein with respect to devices, systems, and methods for modulation of renal nerves using electrodes, other applications and other treatment modalities in addition to those described herein are within the scope of the present technology. Additionally, other embodiments of the present technology can have different configurations, components, or procedures than those described herein. For example, other embodiments can include additional elements and features beyond those described herein or be without several of the elements and features shown and described herein. For ease of reference, throughout this disclosure identical reference numbers are used to identify similar or analogous components or features, but the use of the same reference number does not imply that the parts should be construed to be identical. Indeed, in many examples described herein, the identically-numbered parts are distinct in structure and/or function.

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device. The term "area" as used herein with respect to an electrode refers to a surface area and can refer to a size of a particular surface area, e.g. "fluid-interface area" of an electrode.

Selected Examples of Neuromodulation Systems

FIG. 1 illustrates a neuromodulation system 10 ("system 10") configured in accordance with an embodiment of the present technology. The system 10 can include a neuromodulation catheter 12 operably coupled to a console 26. The catheter 12 can include an elongate shaft 16 having a proximal portion 18, and a distal portion 20. The catheter 12 can further include a neuromodulation element 21 at the distal portion 20 of the shaft 16, and a handle 34 at the proximal portion 18 of the shaft 16. The neuromodulation element 21 can include a support member 24 and one or more wire electrodes 202, 204 wrapped in a helical/spiral configuration around the support member 24. It will be appreciated that although two electrodes 202, 204 are shown, the neuromodulation element 21 can include more or fewer than two electrodes.

The proximal end of the therapeutic assembly 21 is carried by or affixed to the distal portion 20 of the elongate shaft 16. A distal end of the therapeutic assembly 21 may terminate with, for example, an atraumatic rounded tip or cap (e.g., cover 129 in FIG. 5C). Alternatively, the distal end of the therapeutic assembly 21 may be configured to engage another element of the system 10 or treatment device 12. For example, the distal end of the therapeutic assembly 21 may define a passageway for engaging a guide wire (not shown) for delivery of the treatment device using over-the-wire ("OTW") or rapid exchange ("RX") techniques.

The energy source or console 26 can be configured to generate a selected form and/or magnitude of energy for delivery to a target treatment site via the electrodes 202, 204. For example, the console 26 can include an energy generator configured to generate radio frequency (RF) energy, pulsed energy, microwave energy, optical energy, ultrasound energy (e.g., intravascularly delivered ultrasound, extracorporeal ultrasound, high-intensity focused ultrasound (HIFU)), direct heat energy, radiation (e.g., infrared, visible, gamma), or another suitable type of energy. In a particular embodiment, the console 26 includes an RF generator operably coupled to the electrodes 202, 204. The console 26 can be configured to control, monitor, supply, or otherwise support operation of the catheter 12. A control mechanism, such as a foot pedal 32, may be connected (e.g., pneumatically connected or electrically connected) to the console 26 to allow an operator to initiate, terminate and/or adjust various operational characteristics of the energy generator, such as power delivery.

The energy console 26 can be electrically coupled to the neuromodulation (treatment) device 12 via a cable 28. At least one supply wire (not shown) passes along the elongated shaft 16 or through a lumen in the elongated shaft 16 to the one or more wire electrodes 202, 204 and transmits the treatment energy to the one or more wire electrodes 202, 204. In some embodiments, each helical push wire electrode 202, 204 includes its own supply wire which would allow for each helical push wire electrode 202, 204 to be independently energized in a sequential or exclusive manner. In other embodiments, however, the wire electrodes 202, 204 may be electrically coupled to the same supply wire. The supply wire may be used as a thermocouple wire and may be used to transmit temperature and impedance measurements taken at the distal cap.

The console 26 can be configured to deliver neuromodulation energy according to one or more automated control algorithms 30 and/or manually under the control of a clinician. The control algorithms 30 can be executed using a processor (not shown) of the system 10 to control the delivery of power to the neuromodulation element 21. In some embodiments, selection of a control algorithm 30 for a particular patient may be guided by one or more diagnostic algorithms 33 that include measuring and evaluating one or more parameters prior to energy delivery. For example, the diagnostic algorithms 33 can provide patient-specific feedback to a clinician who can use the feedback to select an appropriate control algorithm 30 and/or to modify a previously selected control algorithm 30. Further details regarding control algorithms 30 are described below with reference to FIG. 10. Further details regarding diagnostic algorithms 33 are described below with reference to FIGS. 4 and 6-9.

The electrodes 202, 204 may be configured to deliver power independently (e.g., in a monopolar fashion) simultaneously, selectively, and/or sequentially. Alternatively or in addition, the electrodes 202, 204 may be configured to deliver power collectively (e.g., in a bipolar fashion). In monopolar embodiments, a neutral or dispersive electrode 38 may be electrically connected to the console 26 and attached to the exterior of a patient. Furthermore, a clinician may optionally choose which electrodes 202, 204 are used for power delivery in order to form highly customized lesion(s) having a variety of shapes or patterns.

The system 10 can further include a controller 42 having, for example, memory (not shown), storage devices (e.g., disk drives), one or more output devices (e.g., a display), one or more input devices (e.g., a keyboard, a touchscreen, etc.) and processing circuitry (not shown). The output devices may be configured to transmit signals to the catheter 12 (e.g., via the connector 28) to control power to the electrodes 202, 204. In some embodiments the output devices can be configured to obtain signals from the electrodes 202, 204 and/or any sensors associated with the catheter 12, such as a pressure sensor, temperature sensor, impedance sensor, flow sensor, chemical sensor, ultrasound sensor, optical sensor, or another suitable sensing device. The sensors (not shown) may be located proximate to or within the helical push wire electrodes 22 and connected to one or more supply wires (not shown). For example, a total of two supply wires may be included, in which both wires could transmit the signal from the sensor and one wire could serve dual purpose and also convey the energy to the helical push wire electrodes 22. Alternatively, a different number of supply wires may be used to transmit energy to the helical push wire electrodes 22.

The indicator 40 of the system 10 can serve as an output device and may be a standalone device or may alternatively be associated with the console 26 and/or the handle 34. The indicator 40 can include one or more LEDs, a device configured to produce an audible indication, a display screen, and/or other suitable communicative devices. In some embodiments, the indicator 40 is interactive. For example, the indicator 40 can include a user interface that can receive user input and/or provide information to a user. As another example, the indicator 40 can include processing circuitry for monitoring the one or more sensors. Display devices may be configured to provide indications of power levels or sensor data, such as audio, visual or other indications, or may be configured to communicate the information to another device.

In some embodiments, the controller 42 is part of the console 26, as shown in FIG. 1. Additionally or alternatively, the controller 42 can be personal computer(s), server computer(s), handheld or laptop device(s), multiprocessor system(s), microprocessor-based system(s), programmable consumer electronic(s), digital camera(s), network PC(s), minicomputer(s), mainframe computer(s), and/or any suitable computing environment. The memory and storage devices can be computer-readable storage media that may be encoded with non-transitory, computer-executable instructions (e.g., corresponding to the control algorithm(s) 30, the feedback algorithm(s) 33, etc.). In addition, the instructions, data structures, and message structures may be stored or transmitted via a data transmission medium, such as a signal on a communications link and may be encrypted. Various communications links may be used, such as the Internet, a local area network, a wide area network, a point-to-point dial-up connection, a cell phone network, Bluetooth, RFID, and other suitable communication channels. Some aspects of the system 10 may be described herein in the general context of computer-executable instructions, such as program modules, executed by one or more computers or other devices. Generally, program modules include routines, programs, objects, components, data structures, and so on that perform particular tasks or implement particular abstract data types. The functionality of the program modules may be combined or distributed as desired in various embodiments.

Selected Examples of Neuromodulation Elements and Methods

FIG. 2A is an enlarged side view of the neuromodulation element 21 in a delivery state. As shown in FIG. 2A, the support member 24 of the neuromodulation element 21 can be at least partially positioned within a central lumen of the shaft 16 and have a portion that extends distally from an opening at the distal end of the shaft 16. The first and second electrodes 202, 204 can have proximal ends (not shown) coupled to a proximal portion of the catheter 12 (e.g., at the handle 34) and distal ends coupled to a distal portion of the support member 24. A proximal portion of each of the first and second electrodes 202, 204 can be surrounded by first and second proximal sleeves 212b, 214b, respectively, and a distal portion of each of the first and second electrodes 202, 204 can be surrounded by first and second distal sleeves 212a, 214a, respectively. A segment of each of the electrodes 202, 204 can be exposed (e.g., not surrounded by the sleeves and/or any other structure of the catheter 12) between the proximal 212b, 214b and distal 212a, 214a sleeves. The sleeves 212a-b, 214a-b can be sufficiently flexible to allow the electrodes 202, 204 to radially expand and/or collapse onto the support member 24 yet stiff enough to provide control of the exit and/or entry angles of the electrodes 202, 204.

FIG. 2B is an enlarged side view of the neuromodulation element 21 in a treatment state having a shape wherein electrodes 202 and 204 are helically/spirally intertwined. In the embodiment illustrated in FIG. 2A wherein the neuromodulation element 21 is in a delivery state, electrodes 202 and 204 may also be helically/spirally intertwined, although other arrangements are possible. To transform the neuromodulation element 21 from the delivery state shown in FIG. 2A to the treatment state shown in FIG. 2B, the proximal ends of the electrodes 202, 204 can be pushed distally, thereby causing a distal portion of the electrodes 202, 204 to radially expand. As the electrodes 202, 204 radially expand, the segments 201 of the electrodes 202, 204 between the proximal 212b, 214b and distal 212a, 214a sleeves can increase. For example, as shown in FIG. 2A, when the neuromodulation element 21 is in the delivery state, the segments 201 of the electrodes 202, 204 between the proximal 212b, 214b and distal 212a, 214a sleeves may be relatively small. As shown in FIG. 2B, when the neuromodulation element 21 is in the treatment state, the segments 201 of the electrodes 202, 204 between the proximal 212b, 214b and distal 212a, 214a sleeves may be significantly larger. Thus, moving the neuromodulation element 21 from the delivery state to the treatment state can increase the size of therapeutically active segments of the electrodes 202, 204. Moreover, when the neuromodulation element 21 is in the treatment state, the electrodes can have a shape well suited for making stable contact with an inner wall of a lumen within which the neuromodulation element 21 is disposed. For example, such a lumen can have an uncertain and potentially varying diameter that the neuromodulation element 21 resiliently accommodates.

Figure 3A:
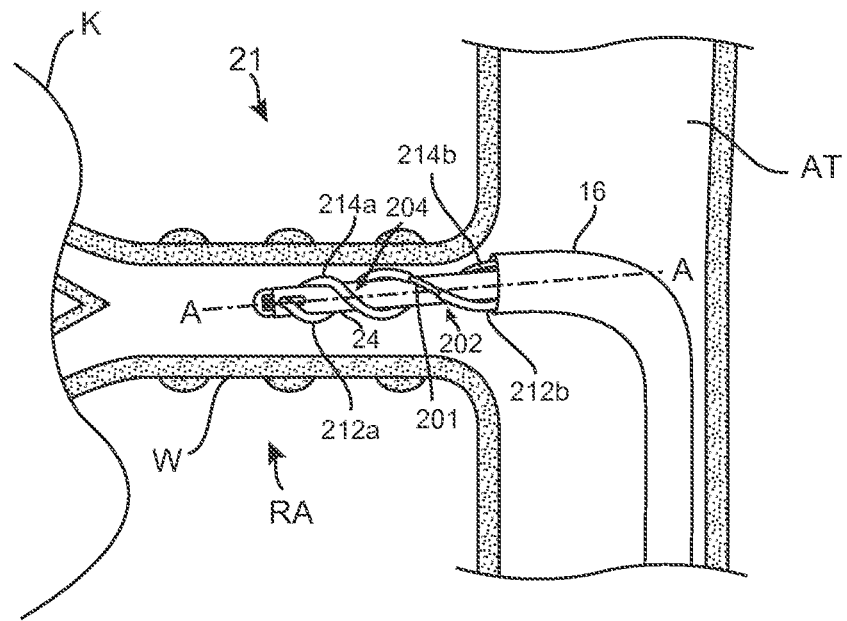
FIG. 3A is a side view of the neuromodulation element of FIG. 1 in the delivery state positioned at a treatment site.

FIG. 3A is an enlarged anatomical side view of the neuromodulation element 21 and associated components in a delivery state being positioned at a treatment location within a renal artery RA that extends between an aorta AT and a kidney K in a human patient. The neuromodulation element 21 can also be used for other purposes and at treatment locations within other suitable body lumens. To locate the neuromodulation element 21 at the treatment location, the catheter 12 can be advanced toward the treatment location while the neuromodulation element 21 is radially constrained in the low-profile delivery state, as shown in FIG. 3A. The shaft 16 may be guided, simultaneously or separately, from a vascular puncture site (not shown) to renal artery RA using a guiding catheter and/or a guide wire, which is omitted from FIG. 3A for simplicity of illustration.

As shown in FIG. 3A, when the neuromodulation element 21 is in the delivery state, at least a portion of the segment 201 of each of the electrodes 202, 204 between the proximal 212b, 214b and distal 212a, 214a sleeves may be exposed to the interior of the renal artery RA. As such, at least a portion of each of the segments 201 defines a fluid-interface area that is in contact with a biological fluid (e.g., blood) present in the renal artery RA at the treatment site. Once the neuromodulation element 21 is adequately positioned at the treatment site, the proximal ends of the electrodes 202, 204 can be pushed distally to begin transformation of the neuromodulation element 21 from its delivery state to its treatment state. As the electrodes 202, 204 radially expand, the segments 201 lengthen. As such, at least before the electrodes 202, 204 contact the wall W of the renal artery RA, while the electrodes 202, 204 expand, the fluid-interface area of each of the electrodes 202, 204 increases and a sleeve-interface area of the electrode (e.g., the portion of the electrode surrounded by the sleeves 212a-b, 214a-b) decreases.

At some point during deployment, the electrodes 202, 204 can begin to contact an inner surface S of the wall W of the renal artery RA. As this occurs, portions of each of the segments 201 previously in contact with biological fluid may instead begin to contact the wall W. Accordingly, a wall-interface area (i.e., the portion of each of the electrodes 202, 204 in contact with the wall W) may increase as the electrodes 202, 204 continue to expand and additional portions of the electrodes 202, 204 engage the wall W. Depending on the rate at which the segments 201 are lengthening and the rate at which the wall-interface area increases, the fluid-interface area and/or the sleeve-interface area of each of the electrodes 202, 204 can increase, decrease, and/or remain the same as the wall-interface area of each of the electrodes 202, 204 increases. For example, since the electrodes may still be expanding when first making contact with the wall W, if the rate at which the electrodes are expanding (and thus exposing additional portions of the electrodes) is greater than the rate at which the wall-interface area increases (rate at which additional portions of the electrodes contact the wall W), then the fluid-interface area may still be increasing.

Figure 3B:
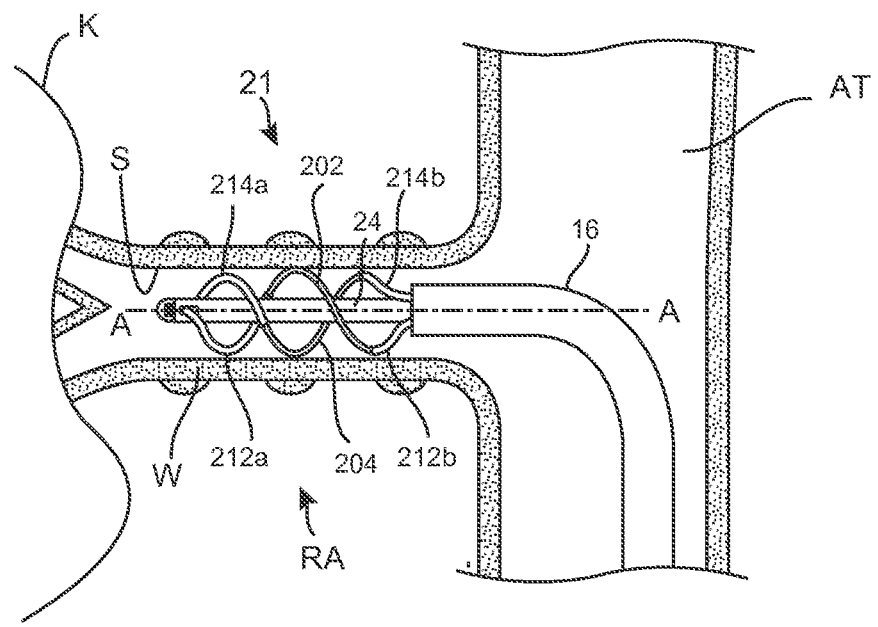
FIG. 3B is a side view of the neuromodulation element of FIG. 1 in the treatment state positioned at the treatment site.

Expansion of the electrodes 202, 204 can end once the electrodes 202, 204 are in stable apposition with an inner surface S of a wall W of the renal artery RA, as shown in FIG. 3B. At this stage of deployment, the segments 201 are no longer increasing in length, and thus both the wall-interface areas, the sleeve-interface areas, and the fluid-interface areas of the electrodes 202, 204 remain generally constant. At this time, one or both of the electrodes 202, 204 can be energized to modulate one or more nerves at or near the treatment location.

Before treatment begins, one or more of the diagnostic algorithms 33 can be used to monitor one or more operating parameters. Such operating parameters detected by the diagnostic algorithm(s) 33 include electrical properties (e.g., impedance, voltage, current, power, etc.), temperature, and/or blood flow parameters as compared to accepted or expected thresholds and/or predetermined or calculated ranges. For example, predetermined operating parameter thresholds and/or ranges can be empirically determined to create a look-up table. The look-up table may provide operating parameter thresholds and/or ranges for corresponding operating threshold values. Look-up table values can be empirically determined, for example, based on clinical studies.

Figure 4:
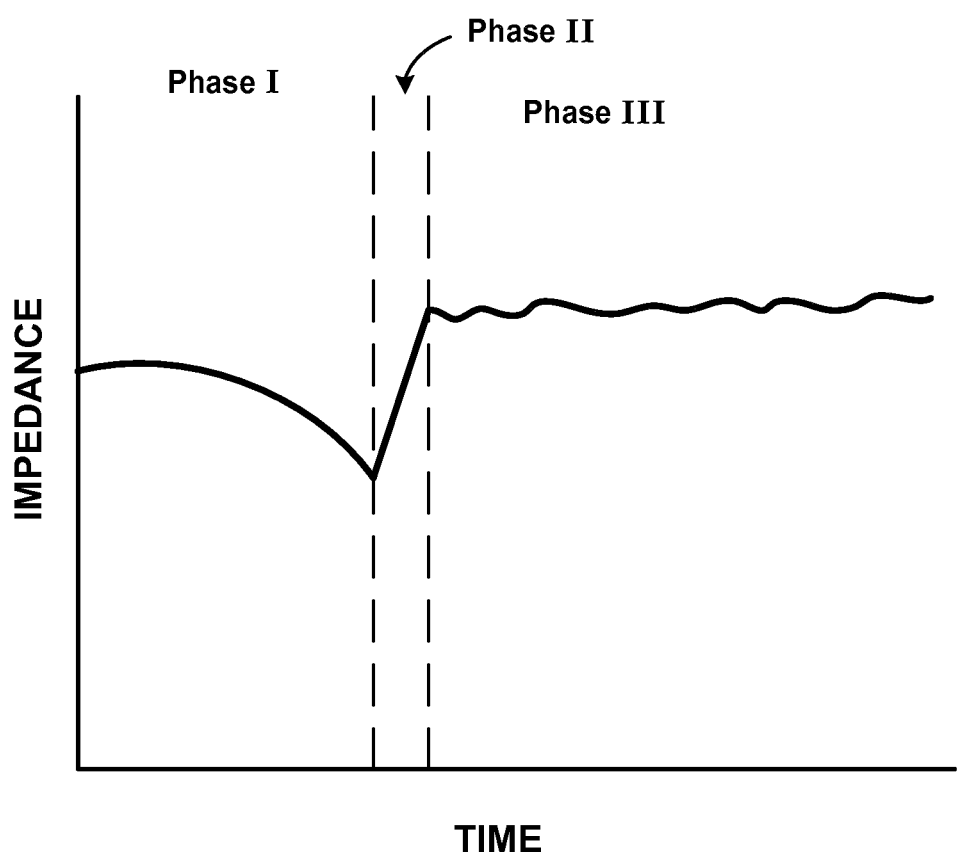
FIG. 4 is a graph of impedance relative to time during delivery and deployment of the neuromodulation element shown in FIGS. 2A-2B.

Impedance is one example of an operating parameter that can be advantageous to monitor for several diagnostic reasons, one of which is to inform the clinician as to the existence and/or degree of contact between one or more of the electrode(s) and the lumen wall at the treatment location. For example, FIG. 4 shows a graph of impedance measurements versus time as the neuromodulation element 21 is delivered and deployed within the lumen. Generally, the measured impedance can be a function of the sum of material adjacent the electrode (e.g., portions of the sleeves 212a-b, 214a-b, portions of the lumen wall, the biological fluid adjacent to the electrode, etc.). In FIG. 4, time t=0 represents a point during delivery/deployment where the neuromodulation element 21 is located within the lumen at the treatment location in a delivery state (such as that shown in FIG. 3A). In the delivery state, only a small portion of each of the electrode(s) 202, 204 is exposed to biological fluid between the proximal 212b, 214b and distal 212a, 214a sleeves, and thus the fluid-interface area for each electrode is relatively low. Because most of the length of the electrode is surrounded by the sleeves 212a-b, 214a-b or other various components of the catheter 12, the measured impedance is relatively high before deployment begins. During a first deployment phase (labeled as "Phase I" in FIG. 4), the electrodes 202, 204 begin to radially expand and the sleeve-interface area decreases. As shown in FIG. 4, during Phase I the measured impedance decreases. This occurs because the impedance of biological fluids tends to be less than that of the sleeves 212a-b, 214a-b and/or other components of the catheter 12 that may be in contact with the electrodes 202, 204 prior to deployment. In another aspect, it can be advantageous to monitor and/or the detect Phase I to evaluate whether or not the electrodes 202, 204 are expanding properly. For example, if one or both electrodes 202, 204 do not deploy properly, the expected impedance decrease would not be reflected in Phase I. As a result, the diagnostic algorithm of the present technology can be configured to identify the generally constant impedance in Phase I and generate a signal to alert the user.

During a second deployment phase (labeled as "Phase II" in FIG. 4), the electrodes 202, 204 begin to contact the lumen wall and impedance measurements increase. This increase in impedance is a result of portions of the fluid-interface area being replaced by wall-interface areas. Lumen walls typically have a higher impedance than biological fluids, and as a result, the measured impedance (which can be a function of the sum of material adjacent the electrode) increases. As shown in FIG. 4, a third deployment phase (labeled as "Phase III") begins when the electrodes 202, 204 have full (or partial) tissue contact with the lumen wall (or in other words, the electrodes 202, 204 have either slowed or stopped expanding) and the wall-interface areas stabilize. As such, the impedance measurements during the third deployment phase may remain generally constant (e.g., not fluctuating beyond about 5 ohms).

It will be appreciated that more or less than three deployment phases are within the scope of the present technology, and the terms "first," "second," and "third" are used only for ease of reference. Moreover, although the graphs shown in FIG. 4 illustrate "increasing" and "decreasing" impedance parabolically and linearly, respectively, impedance measurements can rise and fall along any suitable curve (e.g., exponentially, parabolically, step-wise, other non-linear methods, etc.).

Figure 5A:
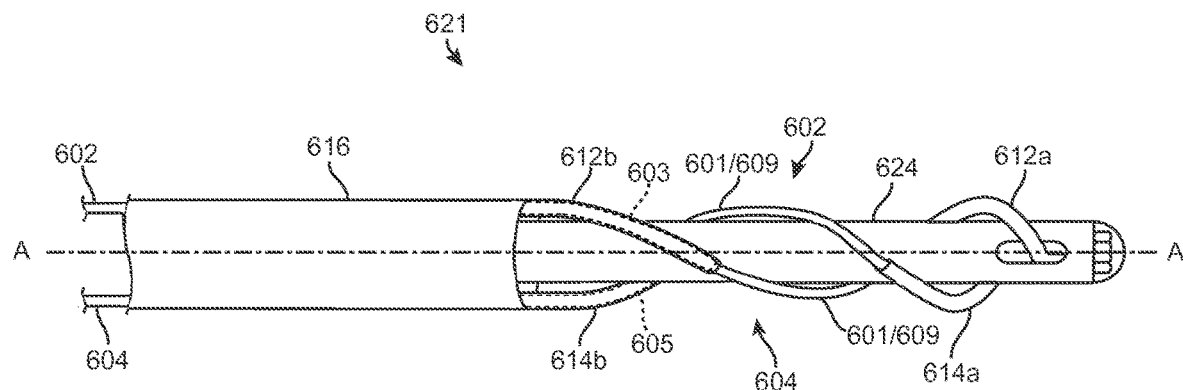
FIG. 5A is a side view of a neuromodulation element in a low-profile delivery state.

FIG. 5A is an enlarged side view of another embodiment of a neuromodulation element 621 in a delivery state. The neuromodulation element 621 can generally relate to the neuromodulation element 21 shown in FIG. 2A, except the first and second electrodes 602, 604 of the neuromodulation element 621 of FIG. 5A include first and second insulated portions 603, 605, respectively (shown in dashed lines). The first and second insulated portions 603, 605 can be at least partially surrounded by (or coated with) an insulation material. As shown in FIG. 5A, in the delivery state, the distal portions of the first and second insulated portions 603, 605 can be surrounded by the first and second proximal sleeves 612b, 614b, respectively, such that the insulated portions 603, 605, do not extend distally beyond the distal ends of their respective sleeves. As such, in the delivery state, the segments 601 of the first and second electrodes 602, 604 between the proximal 612b, 614b and distal 612a, 614a sleeves can be defined by a treatment portion 609 (i.e., the portion of the first and second electrodes 602, 604 configured to deliver energy to the lumen wall). In other embodiments (not shown), a portion of the first and/or second insulated portions 603, 605 can extend beyond the sleeve in the delivery state.

Figure 5B:
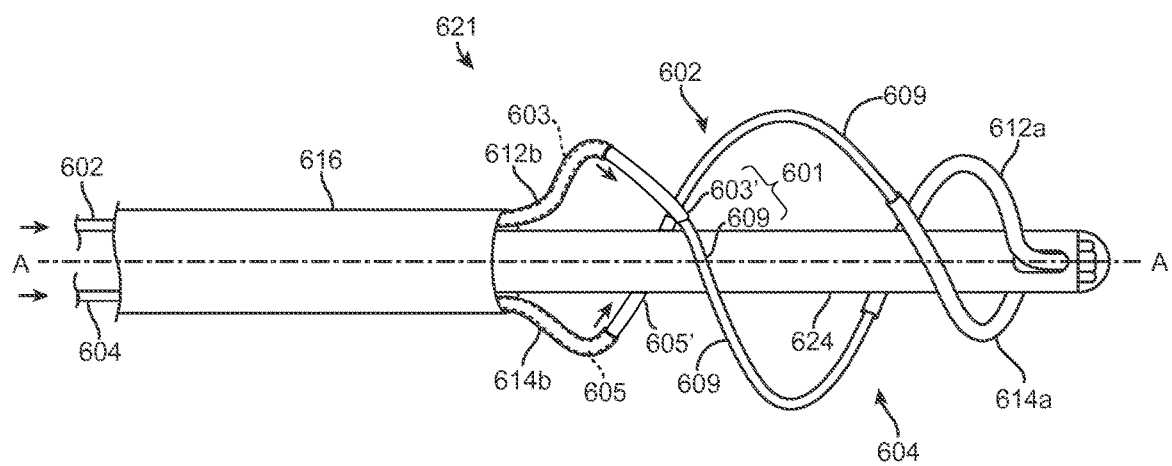
FIG. 5B is a side view of the neuromodulation element of FIG. 5A in an expanded treatment state.

FIG. 5B is an enlarged side view of the neuromodulation element 621 in a treatment state. As illustrated by FIG. 5B, as the electrodes 602, 604 radially expand, the first and second insulated portions 603, 605 are pushed distally and a distal portion 603', 605' of each extends beyond the distal ends of the proximal sleeves 612b, 614b. As such, in the treatment state, the segments 601 of the first and second electrodes 602, 604 between the proximal 612b, 614b and distal 612a, 614a sleeves includes a distal portion 603', 605' of the first and second insulated portions 603, 605 and the treatment portions 609. Accordingly, although the length of the segment 601 between the proximal 612b, 614b and distal 612a, 614a sleeves increases when the neuromodulation element 621 moves from the delivery state to the treatment state, the treatment portions 609 of the electrodes 602, 604 can remain generally the same length. Thus, unlike the neuromodulation element 21 of FIGS. 2A-2B, moving the neuromodulation element 621 from the delivery state to the treatment state generally does not increase the size of the treatment portions 609 of the first and second electrodes 602, 604.

FIG. 5C is a perspective view of a treatment device 112 comprising helical push wire electrodes in a delivery state (e.g., low-profile or collapsed configuration) outside of a patient in accordance with an embodiment of the present technology, and FIG. 5D is a perspective view of the treatment device 112 comprising helical push wire electrodes in a deployed state (e.g., expanded configuration).

Referring to FIGS. 5C and 5D, the distal electrode support structure 122 comprises a tubular member having a central lumen to define a longitudinal axis B-B. In one embodiment, the cross sectional shape of the distal electrode support structure 122 can be a square cross section which may create a smaller profile allowing use with a smaller diameter catheter. In one embodiment, a portion of the distal support structure 122 is square and a portion of the distal support structure 122 is rounded. In another embodiment, the entire distal support structure 122 is square. The illustrated treatment device comprises a shaft 125, one or more helical push wire electrodes 123, a distal electrode support section 122, and thermocouple wires 124. The shaft 125 is mounted to the distal electrode support section 122. A joint may be provided to couple the distal electrode support section 122 to the shaft 125, thereby providing the desired transfer of torque from the shaft 125 to the electrode support section 122 when navigating to the treatment site. More specifically, each end of the electrode support section 122 and the shaft 125 may respectively include mating notches that permit the ends of the tubular members to interlock. In some embodiments, disposed about the joint is a stainless steel sleeve that is crimped about the juncture to provide additional support to the joint. In various embodiments, the shaft 125 is fixed to the distal electrode support section 122 by adhesive, welding, crimping, over-molding, and/or soldering.

The shaft 125 and the distal electrode support section 122 may together define a lumen where the thermocouple wires 124 are disposed. The thermocouple wires 124 are disposed along or in parallel to the longitudinal axis B-B. In one embodiment, the thermocouple wires 124 may be fixed to the proximal end 122a of the distal electrode support section 122. In another embodiment, the thermocouple wires 124 may be fixed to the distal end 122b of the distal electrode support section 122.

In further embodiments, the helical push wire electrodes 123 may be coupled to the thermocouple wires 124 at the distal end 122b of the distal electrode support section 122. The helical push wire electrodes 123 and the thermocouple wires 124 may be coupled by soldering or by a mechanical lock. In one embodiment, the therapeutic assembly may comprise a cover 129 encasing the joint of the helical push wire electrodes and the thermocouple wires. The cover 129 may be made of various materials. In one embodiment, the cover 129 may be coated with Titanium Nitride (TiN). In further embodiments, the therapeutic assembly may comprise a temperature sensor, such as a thermometer. In one embodiment, the cover 129 encloses the temperature sensor. The cover 129 could also be used to electrically connect the supply wire to multiple wire electrodes (such as electrode 123). Accordingly, the same supply wire would also transmit temperature and impedance measurements. In embodiments having only a single electrode (not shown), the same supply wire may act as a TC wire which can transmit temperature and impedance.

Further, as illustrated in FIG. 5D, the proximal sleeves 127 and the distal sleeves 128 may provide complete or near complete insulation of electrodes 123 when the therapeutic assembly is in the delivery configuration with helical push wire electrodes. Accordingly, the impedance of the deployed electrodes is reduced and more RF energy is delivered. In the illustrated example, the proximal sleeves 127 and the distal sleeves 128, or the proximal sleeves 127 and the distal coating or lamination on the electrode 123 have a space between them in the collapsed configuration. In other embodiments, the sleeves 127 and 128, or the proximal sleeves 127 and the distal coating may make contact or even overlap, that is, the distal sleeve 128 or lamination or coating may axially telescope within the lumen of the proximal sleeve 127. In the illustrated example, the electrodes 123 are round wires. In other embodiments, the electrodes 123 may be flat wires or wires of other geometries as previously described. In the case of flat wires, the electrodes 123 can be positioned such that when deployed, the flat surface is in contact with the inner wall of the renal artery. The fixed distal end 123b of the electrodes, the proximal sleeves 127 and the distal sleeves 128 may prevent the flat-wire electrodes from rotating and may ensure that the flat surface is in contact with the inner wall of the renal artery when the electrodes are deployed.

Figure 5E:
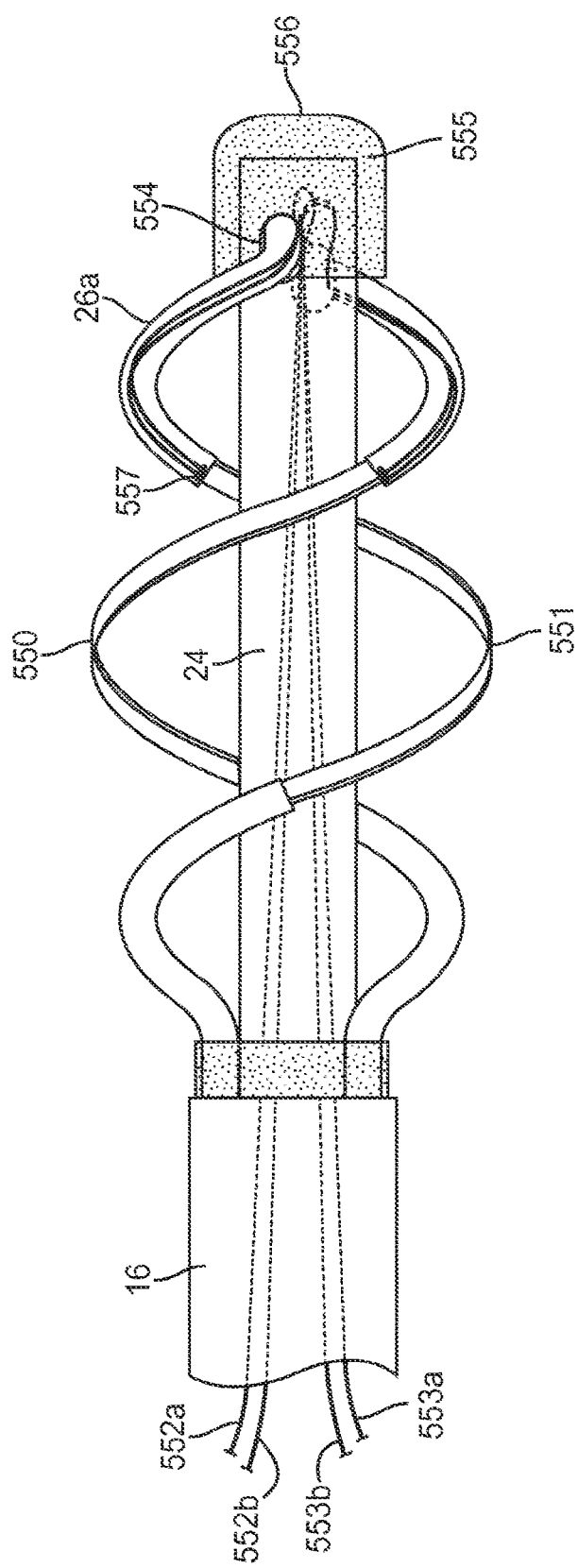
FIG. 5E is a profile view illustrating a therapeutic assembly including push wire electrodes in accordance with an embodiment of the present technology.

FIG. 5E illustrates an exemplary therapeutic assembly comprising push wire electrodes 550 and 551. In this embodiment, a separate TC/supply wire pair 552a-b, 553a-b is coupled to each push wire electrode 550, 551 respectively. In this manner, separate temperature measurements may be obtained and each push wire electrode 550 may be energized independently. One push wire electrode 550 coupled with TC/supply wire pair 552a-b will be described but it should be understood that this same configuration could apply to the other push wire electrode 551 (or any other push wire electrode 550 for an embodiment with a plurality of push wire electrodes).

The TC/supply wire pair 552a-b may run from the proximal end of the treatment device 12 (shown in FIG. 1) through a lumen in the elongated shaft 16 through a central lumen of the distal electrode support section 24 out the push wire electrode's distal exit port 554. The TC/supply wire pair 552a-b runs along the push wire electrode 550 itself being routed across the inner (non-tissue contact) surface of the push wire electrode 550. The TC/supply wire pair 552a-b can be fixed to the push wire electrode 550 at an attachment point 557 near the end of the distal sleeve 26a. Alternatively, the TC/supply wire pair 552a-b can be routed within a lumen of the distal sleeve 26a and fixed to the distal sleeve 26a itself at its end (i.e. exit port of the push wire electrode 550).

The distal tip 556 of the push wire electrode 550 could be covered with adhesive 555 which protects the distal tip, configures the distal tip to be atraumatic, as well as secures the TC/supply wires 552a-b into place. As with previous embodiments, the TC/supply wire pair 552a-b could act as a wire to provide temperature and impedance measurements as well as supply RF energy. Alternatively, RF energy could be supplied to the distal tip with a separate RF supply wire and within the lumen of the catheter, provided the RF supply wire is electrically coupled to the push wire electrode 550.

In an alternative embodiment (not shown), a single TC/supply wire could be provided for a plurality of push wire electrodes. In this embodiment, the push wire electrodes would be electrically coupled within the distal tip thus energizing all push wire electrodes simultaneously. The distal point of attachment of the TC/supply wire to the push wire electrode would be the measurement point of temperature. For certain embodiments, a single temperature measurement on a single push wire electrode could be sufficient.

Accordingly, the TC wires 552a-b would be measuring the temperature of the push wire electrode 550 at a much closer proximity to tissue. In embodiments where the TC wire terminates at the distal tip of the treatment device, the temperature would read near the center of the artery lumen. Reading temperature farther from the target tissue site as well as exposing the tip to a greater amount of blood flow could provide a less accurate tissue temperature, giving more of an estimate of tissue temperature.

When the neuromodulation element 621 is delivered to the renal artery in the delivery state, the radially interior portions of the treatment portions 609 are pressed up against or in full contact with the support member 624. As a result, only portions of the treatment portions 609 are exposed to the interior of the renal artery RA and thus define the fluid-interface area of the electrodes 602, 604. Once the neuromodulation element 621 is adequately positioned at the treatment site, the proximal ends of the electrodes 602, 604 can be pushed distally to begin transformation of the neuromodulation element 621 from its delivery state to its treatment state. As the electrodes 602, 604 radially expand, the treatment portions 609 move away from the support member 624, thereby exposing the previously unexposed portions of the treatment portions 609. During this time, the segments 601 lengthen as the exposed distal portions 603', 605' of the insulated portions 603, 605 increase in length. The treatment portions 609, however, remain generally the same length. As such, at least before the electrodes 602, 604 contact the wall of the renal artery, while the electrodes 602, 604 expand, the fluid-interface area of each of the electrodes 602, 604 can remain generally the same.

At some point during deployment, the first and second electrodes 602, 604 can begin to contact an inner surface of the wall of the renal artery. As this occurs, portions of each of the treatment portions 609 previously in contact with biological fluid may instead begin to contact the wall. Accordingly, a wall-interface area (i.e., the portion of each of the treatment portions 609 in contact with the wall) may increase as the electrodes 602, 604 continue to expand and additional portions of the treatment portions 609 engage the wall. For example, wall-interface areas 123c are illustrated in FIG. 5D with the renal artery wall omitted for clarity. Expansion of the electrodes 602, 604 can end once the electrodes 602, 604 are in stable apposition with an inner surface of a wall of the renal artery. At this stage of deployment, the segments 601 are no longer increasing in length, and thus both the wall-interface areas and the fluid-interface areas of the electrodes 602, 604 remain generally constant. At this time, one or both of the electrodes 602, 604 can be energized to modulate one or more nerves at or near the treatment location via the treatment portions 609.

Figure 6:
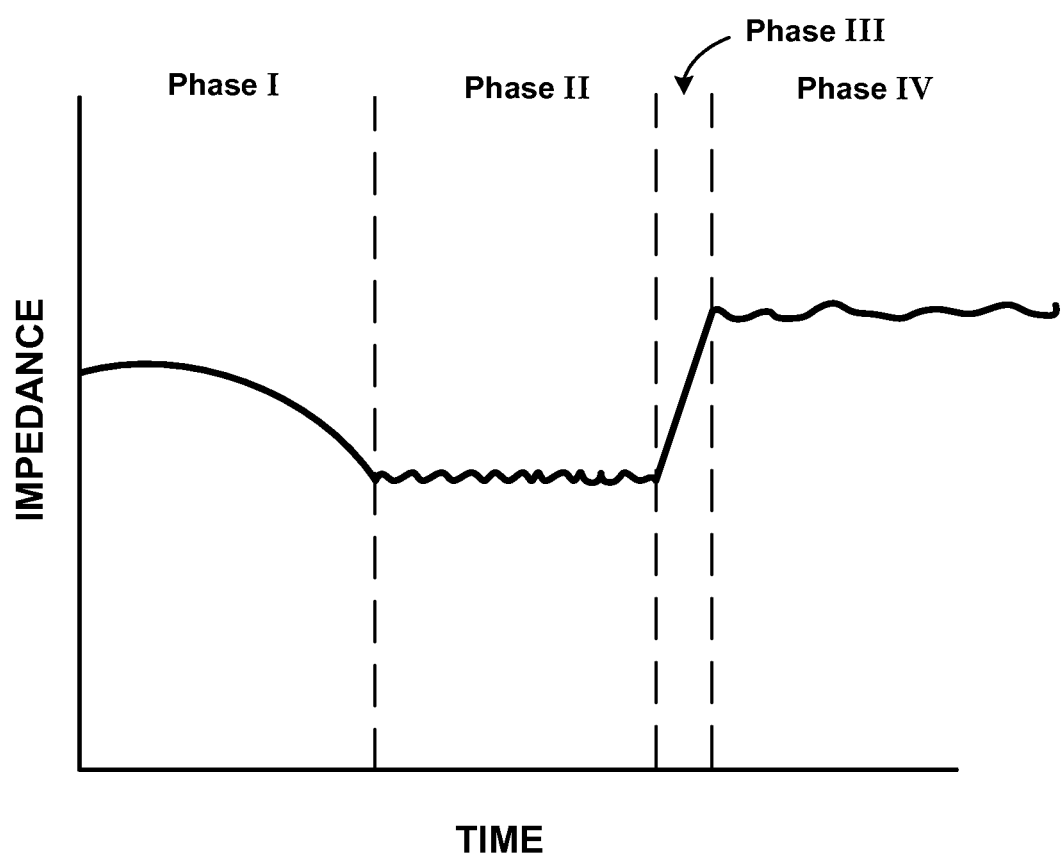
FIG. 6 is a graph of impedance relative to time during delivery and deployment of the neuromodulation element shown in FIGS. 5A-5E.

FIG. 6 shows a graph of impedance measurements versus time as the neuromodulation element 621 is delivered and deployed within the lumen. In FIG. 6, time t=0 represents a point during delivery/deployment where the neuromodulation element 621 is located within the lumen at a treatment location in a delivery state. In the delivery state, only the portions of the treatment portions 602, 604 not in contact with the support member 624 are exposed to biological fluid, and most of the length of the electrode is surrounded by the sleeves 612a-b, 614a-b, insulation material, or other various components of the catheter 12. As such, the measured impedance is relatively high before deployment begins. During a first deployment phase (labeled as "Phase I" in FIG. 6), the electrodes 602, 604 begin to radially expand and the treatment portions 609 move away from the support member 624, thereby exposing the previously unexposed portions of the treatment portions 609 and increasing the fluid-interface area of the electrodes. During this time the measured impedance decreases, as the impedance of biological fluids tends to be less than that of the sleeves 612a-b, 614a-b, insulation material and/or other components of the catheter 12 that may be in contact with the electrodes 602, 604 prior to deployment.

A second phase of deployment (labeled as "Phase II" in FIG. 6) can begin when the electrodes have expanded to a point where the treatment portions 609 are no longer in contact with the support member 624. During the second phase, the electrodes continue to expand and the segments 601 lengthen. The fluid-interface area, however, remains generally constant. This is because the treatment portions 609 remain generally the same length during electrode expansion and the added length of the segment 601 is insulated and does not factor into the fluid-interface area. As such, during this second phase, the fluid-interface area is generally stable, and the impedance is generally stable.

During a third deployment phase (labeled as "Phase III" in FIG. 6), the treatment portions 609 of the electrodes 602, 604 begin to contact the lumen wall and impedance measurements increase. This increase in impedance is a result of portions of the fluid-interface area being replaced by wall-interface areas. Lumen walls typically have a higher impedance than biological fluids, and as a result, the measured impedance (which can be a function of the sum of material adjacent the electrode) increases. As shown in FIG. 6, a fourth deployment phase (labeled as "Phase IV") begins when the electrodes 602, 604 have stopped radially expanding and the wall-interface areas stabilize. As such, the impedance measurements during the fourth deployment phase may remain generally constant.

It will be appreciated that more or less than four deployment phases are within the scope of the present technology, and the terms "first," "second," "third," and "fourth" are used only for ease of reference. Moreover, although the graphs shown in FIG. 4 illustrate "increasing" and "decreasing" impedance parabolically and linearly, respectively, impedance measurements can rise and fall along any suitable curve (e.g., exponentially, parabolically, step-wise, other non-linear methods, etc.).

Figure 7:
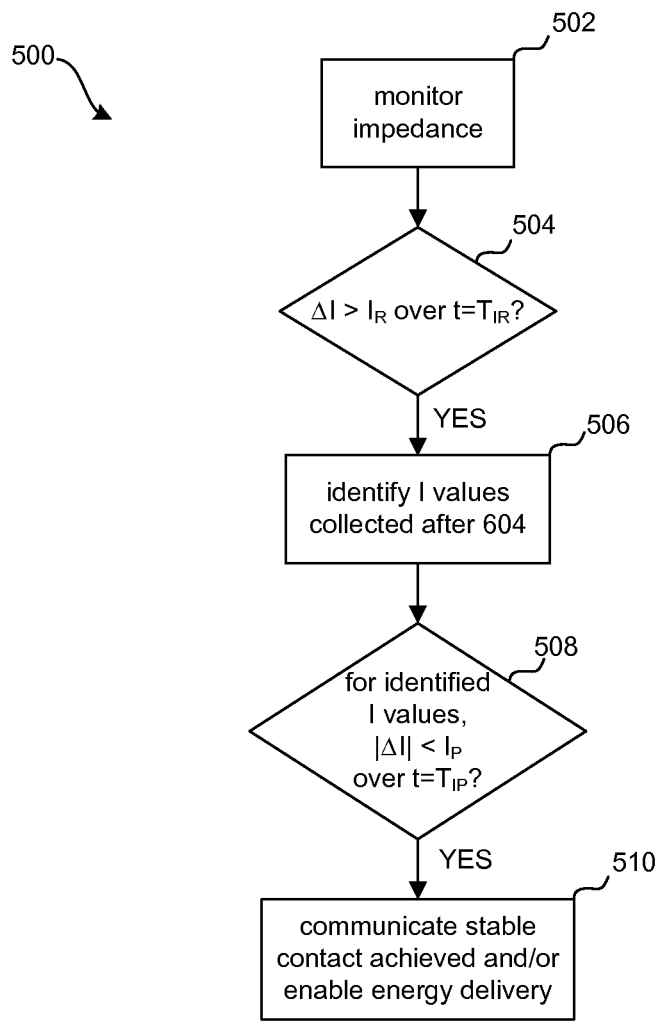
FIG. 7 is a block diagram illustrating an algorithm for evaluating electrode contact for a single electrode in accordance with an embodiment of the present technology.

Based on the above-described relationships between deployment and impedance, one or more diagnostic algorithms can be used to detect stable contact between one or more of the electrodes and the lumen wall prior to initiating treatment and/or to provide feedback to a clinician as to the status of the contact. For example, FIG. 7 is a block diagram illustrating a diagnostic algorithm 500 for determining tissue contact for a single wire electrode in accordance with an embodiment of the present technology. The diagnostic algorithm 500 includes monitoring impedance (block 502) and detecting an increase in impedance above a predetermined threshold IR that lasts for a predetermined amount of time $T_{IR}$ (block 504) (e.g., $\Delta I \geq 40$ ohms over $T_{IR}=2$ seconds). Should a sufficient increase in impedance be detected, the algorithm 500 can include evaluating the impedance measurements collected after the detected increase (e.g., within 1 to 2 ms) and determining whether the detected increase is followed by generally stable (e.g., constant) impedance readings for a predetermined amount of time. For example, as shown in block 506, the algorithm 500 can include identifying the impedance measurements (or set of impedance measurements) collected after the detected impedance increase and determining whether, within those measurements, the absolute change in impedance is below a predetermined threshold $I_P$ over the course of a predetermined amount of time $T_{IP}$ (e.g., $|\Delta I|\leq 5$ ohms over $T_{IP}=10$ seconds.) As such, the algorithm 500 can include detecting a transition in impedance measurements between Phase II and Phase III that corresponds to a stabilization of the wall-interface area. Such a stabilization can indicate stable contact between the electrode and the lumen wall, and the algorithm 500 can include causing the indicator 40 (FIG. 1) to communicate to the user that stable contact has been achieved. In some embodiments, the algorithm 500 can include communicating to stop expanding the electrodes or cause an electro-mechanical actuator in the handle to stop expanding the electrodes. Additionally or alternatively, the algorithm 500 can include causing the system 10 to initiate energy delivery and/or otherwise enable the system 10 to initiate energy delivery via the electrode.

Figure 8:
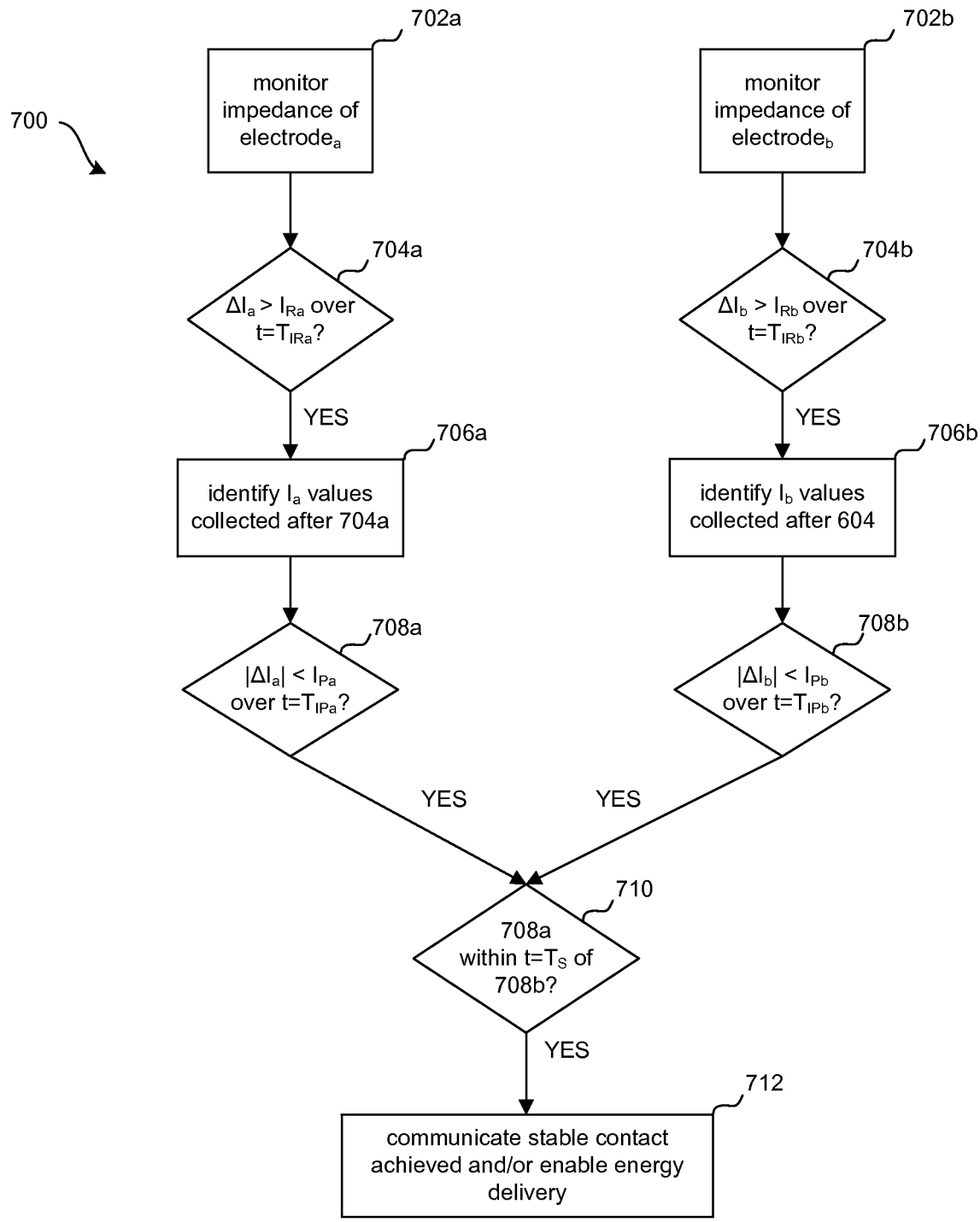
FIG. 8 is a block diagram illustrating an algorithm for evaluating electrode contact for multiple electrodes in accordance with an embodiment of the present technology.

FIG. 8 is a block diagram illustrating a diagnostic algorithm 700 for determining tissue contact for a neuromodulation element 21 having multiple electrodes in accordance with an embodiment of the present technology. Although the algorithm 700 is described with reference to two electrodes (referred to and labeled as electrode$_a$ and electrode$_b$ for ease of reference), the algorithm 700 can be used with more than two electrodes. Blocks 702a-708a corresponds with electrode$_a$ and 708a-708b corresponds with electrode$_b$, the description of which generally relate to blocks 602-608 described above with reference to FIG. 5. As shown in FIG. 8, the algorithm 700 can include enabling energy delivery (block 712) only if stable contact is detected for electrode$_a$ within a predetermined time $T_S$ of electrode$_b$ (e.g., stable contact for electrode$_a$ occurs within 1 second of electrode$_b$) (block 710). It can be advantageous to detect stable contact for all of the electrodes of the neuromodulation element before enabling energy delivery since not all of the electrodes will necessarily achieve stable contact. For example, electrode$_a$ may deploy and reach stable contact with the lumen wall while electrode$_b$ does not have stable contact (e.g., because of an obstruction or entanglement with a component of the catheter, as a result of the local anatomy, etc.). In other embodiments, the algorithm 700 can include enabling energy delivery regardless of the timing of detection for electrode$_a$ and electrode$_b$. For example, where stable contact is detected only for electrode$_a$, energy can be delivered only to electrode$_a$ and not electrode$_b$. In yet other embodiments, the electrodes can be monitored separately and energy can be delivered only to whichever electrode has achieved stable contact.

Selection of Customized Algorithms Based on Pre-Neuromodulation Feedback

Before treatment begins, one or more diagnostic algorithms 33 can detect certain patient attribute(s) which denote a possibility that one or more of the control algorithm(s) 30 will not provide efficacious treatment to the particular patient and/or adequately evaluate patient-specific physiological parameters in response to neuromodulation. Such patient attributes detected by the diagnostic algorithm(s) 33 can include, for example, the inner diameter of the body lumen at the treatment location, that are outside of accepted or expected thresholds and/or predetermined or calculated ranges. Accordingly, evaluation of certain patient attributes by the diagnostic algorithm(s) 33 prior to beginning treatment can inform the clinician as to which control algorithm(s) 30 are most likely to provide successful neuromodulation to the individual patient. The diagnostic algorithm(s) 33 can indicate a particular control algorithm 30 via the indicator 40 based on the patient profile developed by the diagnostic algorithm 33 and/or the diagnostic algorithm 33 can cause the patient profile to be displayed or indicated to the clinician so that the clinician can make an informed selection of the appropriate control algorithm 30 and/or modification of the control algorithm 30. In some instances, the diagnostic algorithm 33 may indicate that the patient is not a good candidate for neuromodulation and the clinician may decide not to pursue treatment.

The inner diameter of the lumen at the treatment location can often be an important patient attribute since it can inform the clinician as to the appropriate control algorithm 30 or energy delivery profile to utilize during treatment. Lumen inner diameters can vary from patient to patient, and as a result, a standardized control algorithm(s) 30 may not be appropriate across all treatments. For example, if a patient has relatively large lumen inner diameter, the energy delivered may not reach a predetermined maximum power level before a predetermined treatment time expires (and before the tissue can be adequately heated by the electrodes). If a patient has relatively small lumen inner diameter, the electrode(s) can heat up too quickly. Accordingly, disclosed herein are one or more diagnostic algorithms 33 that determine contact prior to initiating treatment and provide feedback to the clinician as to selection and/or modification of the control algorithm 30.

Figure 9:
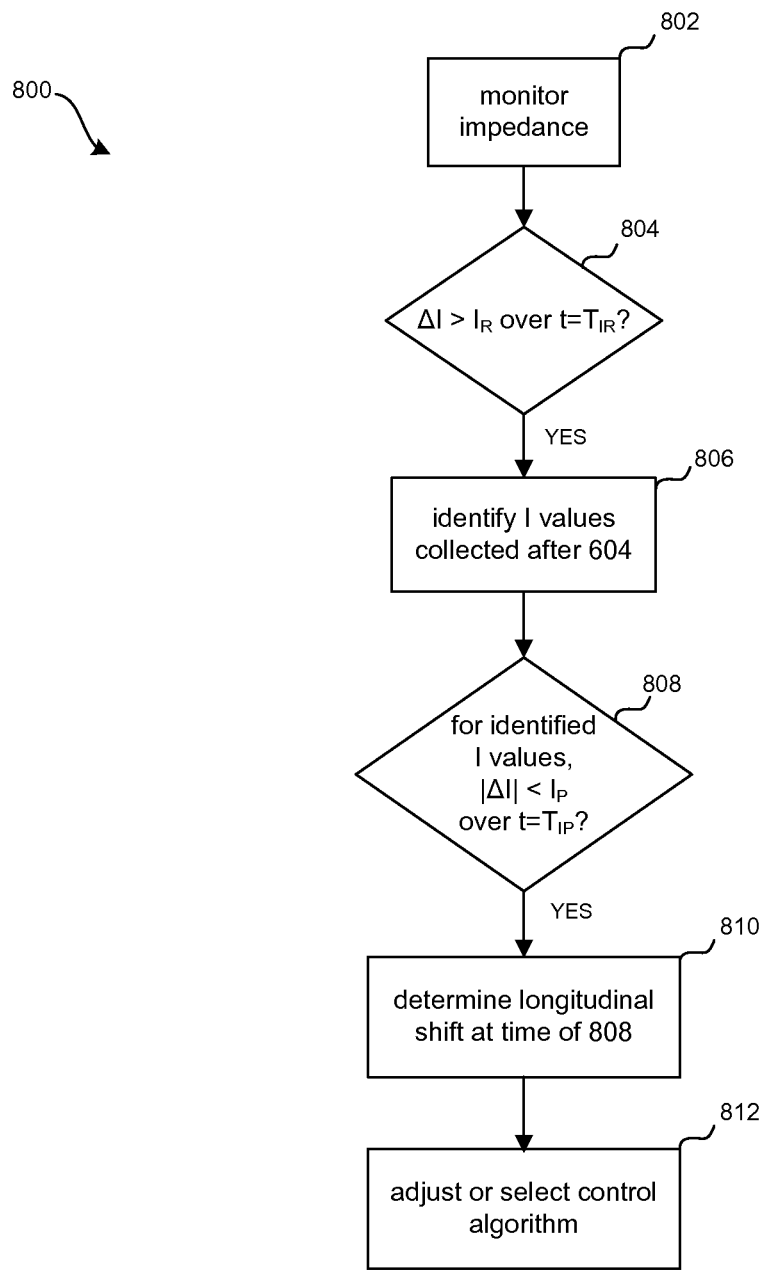
FIG. 9 is a block diagram illustrating an algorithm for determining an inner diameter of a lumen at a treatment site in accordance with an embodiment of the present technology.

FIG. 9 is a block diagram illustrating a diagnostic algorithm 800 for determining lumen inner diameter at the treatment location in accordance with an embodiment of the present technology. The description of blocks 802-808 generally correspond to blocks 602-608 of FIG. 5. In some embodiments, the catheter 12 (FIG. 1) can include a gauge (not shown) coupled to one or more electrodes and configured to measure the longitudinal shift of the electrode(s) relative to the shaft during deployment. As shown in block 810, at the time stable contact between the electrode and lumen wall is detected, the longitudinal shift of the electrode can be measured. The measured longitudinal shift of the electrode can then be used to determine the inner diameter of the lumen at the treatment site based on predetermined data that correlates various longitudinal shift values to lumen inner diameter values. Based on the lumen inner diameter, the algorithm 800 can include selecting an appropriate control algorithm or adjusting the existing control algorithm. In some embodiments, the user can manually select the appropriate control algorithm based on the feedback. The control algorithm 30 can be adjusted (or the appropriate control algorithm selected) to have a direct or indirect linear relationship such that a greater amount of energy is delivered when the longitudinal shift at the time of detection of stable contact is relatively large. Likewise, the control algorithm 30 can be adjusted (or the appropriate control algorithm selected) such that a lesser amount of energy is delivered when the longitudinal shift at the time of detection of stable contact is relatively small. Additionally or alternatively, the control algorithm 30 can be adjusted (or the appropriate control algorithm selected) to have a direct or indirect linear relationship such that energy is delivered for a longer time period when the longitudinal shift at the time of the transition of the electrical property is relatively large. Likewise, the control algorithm 30 can be adjusted (or the appropriate control algorithm selected) such that a shorter time period when the longitudinal shift at the time of the transition of the electrical property is relatively small.

Selected Embodiments of Energy Delivery Profiles

With the treatments disclosed herein for delivering neuromodulation treatment to target tissue, it may be beneficial for energy to be delivered to the target neural structures in a controlled manner. The controlled delivery of energy will allow the zone of thermal treatment to extend into the renal fascia while reducing undesirable energy delivery or thermal effects to the lumen wall. A controlled delivery of energy may also result in a more consistent, predictable and efficient overall treatment. Accordingly, the console 26 desirably includes a controller 42 (FIG. 1) including a memory component with instructions for executing a control algorithm 30 for controlling the delivery of power and energy to the energy delivery device.

Figure 10:
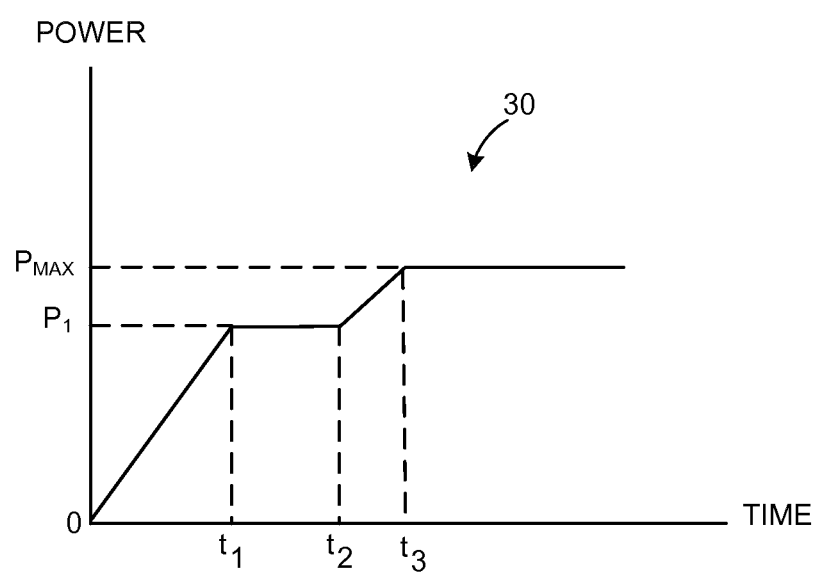
FIG. 10 is a graph of power relative to time for a control algorithm in accordance with an embodiment of the present technology.

For example, FIG. 10 illustrates one example of a control algorithm 30 configured in accordance with an embodiment of the present technology. When a clinician initiates treatment, the control algorithm 30 includes instructions to the console 26 to gradually adjust its power output to a first power level $P_1$ (e.g., 4 watts) over a first time period $t_1$ (e.g., 15 seconds). The power can increase generally linearly during the first time period. As a result, the console 26 increases its power output at a generally constant rate of $P_1/t_1$. Alternatively, the power may increase exponentially, parabolically, step-wise, and/or other non-linear methods. Once $P_1$ and $t_1$ are achieved, the algorithm may hold at P1 until a new time t2 for a predetermined period of time $t_2-t_1$ (e.g., 1 second). At $t_2$ power is increased by a predetermined rate (e.g., 0.5 watts/seconds) to a maximum power $P_{MAX}$ (e.g., 6 watts, 10 watts, etc.) over a predetermined period of time, $t_3-t_2$ (e.g., 1 second). In other embodiments, the control algorithm 30 applies the maximum power $P_{MAX}$ immediately upon initiation of energy delivery and maintains $P_{MAX}$ for the total treatment time (e.g., up to about 120 seconds) and/or steps down the power from $P_{MAX}$ during the remainder of treatment. Although the control algorithm 30 of FIG. 10 comprises a power-control algorithm, it should be understood that the control algorithm 30 additionally or alternatively may include temperature control and/or current control. For example, power may be initiated when a combination of impedance requirements and temperature requirements are met, power may be gradually increased until a desired temperature (or temperatures) is obtained for a desired duration (or durations), or power may be ceased when a threshold temperature or specific impedance change is measured.

The control algorithm 30 also can include continuously and/or periodically monitoring certain operating parameters such as time, electrical properties (e.g., impedance, voltage, current, power, etc.) and/or other suitable parameters. The control algorithm 30 can also include calculating and/or monitoring derivatives of such operating parameters, such as impedance over a specified time, a maximum impedance, a maximum average impedance, a minimum impedance, an impedance at a predetermined or calculated time relative to a predetermined or calculated impedance, an average impedance over a specified time, and other suitable derivatives. As used herein, "operating parameters" includes operating parameter measurements, derivatives, manipulations, etc. Measurements may be taken at one or more predetermined times, ranges of times, calculated times, and/or times when or relative to when a measured event occurs.

Renal Neuromodulation

Renal neuromodulation is the partial or complete incapacitation or other effective disruption of nerves innervating the kidneys (e.g., rendering neural fibers inert or inactive or otherwise completely or partially reduced in function). For example, renal neuromodulation can include inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). Renal neuromodulation is expected to efficaciously treat several clinical conditions characterized by increased overall sympathetic activity, and, in particular, conditions associated with central sympathetic overstimulation such as hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, osteoporosis, and sudden death, among others. The reduction of afferent neural signals typically contributes to the systemic reduction of sympathetic tone/drive, and renal neuromodulation is expected to be useful in treating several conditions associated with systemic sympathetic overactivity or hyperactivity. Renal neuromodulation can potentially benefit a variety of organs and bodily structures innervated by sympathetic nerves.

Thermal effects can include both thermal ablation and non-ablative thermal alteration or damage (e.g., via sustained heating and/or resistive heating) to partially or completely disrupt the ability of a nerve to transmit a signal. Desired thermal heating effects, for example, may include raising the temperature of target neural fibers above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for ablative thermal alteration. More specifically, exposure to thermal energy in excess of a body temperature of about 37° C., but below a temperature of about 45° C., may induce thermal alteration via moderate heating of target neural fibers or of vascular structures that perfuse the target fibers. In cases where vascular structures are affected, the target neural fibers may be denied perfusion resulting in necrosis of the neural tissue. For example, this may induce non-ablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures that perfuse the target fibers. In some patients, it may be desirable to achieve temperatures that thermally ablate the target neural fibers or the vascular structures, but that are less than about 90° C., or less than about 85° C., or less than about 80° C., and/or less than about 75° C. Other embodiments can include heating tissue to a variety of other suitable temperatures. Regardless of the type of heat exposure utilized to induce the thermal neuromodulation, a therapeutic effect (e.g., a reduction in renal sympathetic nerve activity (RSNA)) is expected.

Various techniques can be used to partially or completely incapacitate neural pathways, such as those innervating the kidneys. The purposeful application of energy (e.g., RF energy, mechanical energy, acoustic energy, electrical energy, thermal energy, etc.) to tissue and/or the purposeful removal of energy (e.g., thermal energy) from tissue can induce one or more desired thermal heating and/or cooling effects on localized regions of the tissue. The tissue, for example, can be tissue of the renal artery and adjacent regions of the renal plexus, which lay intimately within or adjacent to the adventitia of the renal artery. For example, the purposeful application and/or removal of energy can be used to achieve therapeutically effective neuromodulation along all or a portion of the renal plexus.

V. Further Examples

The following examples are illustrative of several embodiments of the present technology:

1. A method, comprising:
    advancing a catheter including an elongate shaft and a neuromodulation element operably connected to the shaft toward a treatment location within a body lumen of a human patient, the neuromodulation element including an elongate electrode slidably disposed within a dielectric sleeve;
    deploying the neuromodulation element from a delivery state to a treatment state after advancing the catheter, deploying the neuromodulation element including—
        a first deployment phase during which the electrode moves radially outward while a first interface area between the electrode and the dielectric sleeve decreases and a second interface area between the electrode and a biological fluid at the treatment location increases,
        a second deployment phase following the first deployment phase, the first interface area decreasing and a third interface area between the electrode and a lumen wall at the treatment location increasing during the second deployment phase, and
        a third deployment phase following the second deployment phase, wherein during the third deployment phase the third interface area more stable than it is during the second deployment phase; and
    using the electrode to measure an electrical property of a sum of material adjacent to the electrode while deploying the neuromodulation element, the sum of material adjacent to the electrode including portions of the dielectric sleeve, the lumen wall and the biological fluid adjacent to the electrode;
    detecting a transition of the electrical property corresponding to a transition from the second deployment phase to the third deployment phase; and
    generating a status indication, enabling a neuromodulation treatment, or both in response to detecting the transition of the electrical property.

2. The method of example 1 wherein the electrical property is impedance.

3. The method of example 1 or example 2 wherein detecting the transition of the electrical property includes detecting a transition of a rate of change of the electrical property.

4. The method of example 1 or example 2 wherein detecting the transition of the electrical property includes:
    detecting a rate of change of the electrical property to be greater than a first threshold rate of change for a first time period; and
    detecting the rate of change of the electrical property to be less than a second threshold rate of change for a second time period after the first time period.

5. The method of any of examples 1-4 wherein the electrode is a wire electrode.

6. The method of example 5 wherein the wire electrode is at least generally helical during the third deployment phase.

7. The method of any of examples 1-6 wherein deploying the neuromodulation element includes pushing a proximal end of the electrode in a distal direction.

8. A method, comprising:
    advancing a catheter including an elongate shaft and a neuromodulation element operably connected to the shaft toward a treatment location within a body lumen of a human patient, the neuromodulation element including a first elongate electrode slidably disposed within a first dielectric sleeve and a second elongate electrode slidably disposed within a second dielectric sleeve;
    deploying the first electrode after advancing the catheter, deploying the first electrode including—
        a first deployment phase during which the first electrode moves radially outward while a first interface area of the first electrode between the first electrode and the first dielectric sleeve decreases and a second interface area of the first electrode between the first electrode and a biological fluid at the treatment location increases,
        a second deployment phase following the first deployment phase of deploying the first electrode, the first interface area of the first electrode decreasing and a third interface area of the first electrode between the first electrode and a lumen wall at the treatment location increasing during the second deployment phase of deploying the first electrode, and
        a third deployment phase following the second deployment phase of deploying the first electrode, wherein during the third deployment phase of
    deploying the first electrode the third interface area of the first electrode is more stable than it is during the second deployment phase of deploying the first electrode; and
    deploying the second electrode after advancing the catheter, deploying the second electrode including—
        first deployment phase during which the second electrode moves radially outward while a first interface area of the second electrode between the second electrode and the second dielectric sleeve decreases and a second interface area of the second electrode between the second electrode and the biological fluid at the treatment location increases,
        a second deployment phase following the first deployment phase of deploying the second electrode, the second interface are of the second electrode decreasing and a third interface area of the second electrode between the electrode and the lumen wall at the treatment location increasing during the second deployment phase of deploying the second electrode, and
        a third deployment phase following the second deployment phase of deploying the second electrode, wherein during the third deployment phase of deploying the second electrode while the third interface area of the second electrode is more stable than it is during the second deployment phase of deploying the second electrode; and
    using the first electrode to measure a first electrical property of a first sum of material adjacent to the first electrode while deploying the neuromodulation element, the first sum of material adjacent to the first electrode including portions of the first dielectric sleeve, the lumen wall and the biological fluid adjacent to the first electrode;
    using the second electrode to measure a second electrical property of a second sum of material adjacent to the second electrode while deploying the neuromodulation element, the second sum of material adjacent to the second electrode including portions of the second dielectric sleeve, the lumen wall and the biological fluid adjacent to the second electrode;
detecting a transition of the first electrical property corresponding to a transition from the second deployment phase of deploying the first electrode to the third deployment phase of deploying the first electrode;
detecting a transition of the second electrical property corresponding to a transition from the second deployment phase of deploying the second electrode to the third deployment phase of deploying the second electrode; and
generating a status indication, enabling a neuromodulation treatment, or both in response to detecting the transition of the first electrical property, second electrical property, or both.

9. The method of example 8 wherein generating a status indication, enabling a neuromodulation treatment, or both is in response to detecting an intervening time period between the transition of the first electrical property and the transition of the second electrical property that is less than a threshold time period.

10. The method of example 8 or example 9 wherein:
the first electrical property is a first impedance; and
the second electrical property is a second impedance.

11. The method of any of examples 8-10 wherein:
detecting the transition of the first electrical property includes detecting a transition of a rate of change of the first electrical property; and
detecting the transition of the second electrical property includes detecting a transition of a rate of change of the second electrical property.

12. The method of any of examples 8-10 wherein:
detecting the transition of the first electrical property includes—
  detecting a rate of change of the first electrical property to be greater than a first threshold rate of change for a first time period; and
  detecting the rate of change of the first electrical property to be less than a second threshold rate of change for a second time period after the first time period; and
detecting the transition of the second electrical property includes—
  detecting a rate of change of the second electrical property to be greater than a third threshold rate of change for a third time period; and
  detecting the rate of change of the second electrical property to be less than a fourth threshold rate of change for a fourth time period after the third time period.

13. The method of example 12 wherein:
the first and third threshold rates of change are the same;
the first and third time periods are the same;
the second and fourth threshold rates of change are the same; and
the second and fourth time periods are the same.

14. The method of any of examples 8-13 wherein:
the first electrode is a first wire electrode; and
the second electrode is a second wire electrode.

15. The method of example 14 wherein:
the first wire electrode is at least generally helical during the third deployment phase of deploying the first wire electrode; and
the second wire electrode is at least generally helical during the third deployment phase of deploying the second wire electrode.

16. The method of example 15 wherein the first and second wire electrodes are helically intertwined during the third deployment phase of deploying the first wire electrode and during the third deployment phase of deploying the second wire electrode.

17. A method, comprising:
advancing a catheter including an elongate shaft and a neuromodulation element operably connected to the shaft toward a treatment location within a body lumen of a human patient, the neuromodulation element including an elongate electrode slidably disposed within a dielectric sleeve;
moving an elongate control member relative to the shaft, moving the shaft relative to the control member, or both so as to cause a longitudinal shift between the control member and the shaft and thereby cause the electrode to move radially outward while a wall-interface area between the electrode and a lumen wall at the treatment location increases;
measuring the longitudinal shift while moving the control member;
using the electrode to measure an electrical property of a sum of material adjacent to the electrode while the electrode moves radially outward, the sum of material adjacent to the electrode including portions of the dielectric sleeve, the lumen wall and the biological fluid adjacent to the electrode,
detecting a transition of the electrical property corresponding to a stabilization of the wall-interface area; and
delivering energy to one or more nerves of the patient via the electrode according to a profile of energy over time, the profile being based on the longitudinal shift at the time of the transition of the electrical property, the longitudinal shift at the time of the transition of the electrical property corresponding to a diameter of the body lumen.

18. The method of example 17 wherein delivering energy to the one or more nerves via the electrode includes delivering a greater amount of energy to the one or more nerves when the longitudinal shift at the time of the transition of the electrical property is relatively large and delivering a lesser amount of energy to the one or more nerves when the longitudinal shift at the time of the transition of the electrical property is relatively small.

19. The method of example 17 wherein delivering energy to the one or more nerves via the electrode includes delivering energy to the one or more nerves for a longer time period when the longitudinal shift at the time of the transition of the electrical property is relatively large and energy to the one or more nerves for a shorter time period when the longitudinal shift at the time of the transition of the electrical property is relatively small.

20. The method of any of examples 17-19, further including indicating the diameter of the body lumen.

21. A method, comprising:
advancing a catheter including an elongate shaft and a neuromodulation element operably connected to the shaft toward a treatment location within a body lumen of a human patient, the neuromodulation element including an elongate electrode slidably disposed within a dielectric sleeve;

deploying the neuromodulation element from a delivery state to a treatment state after advancing the catheter, deploying the neuromodulation element including—
  a first deployment phase during which the electrode moves radially outward while a first interface area between the electrode and a biological fluid at the treatment location increases,
  a second deployment phase following the first deployment phase, wherein the first interface area is generally constant during the second deployment phase;
  a third deployment phase following the second deployment phase, the first interface area decreasing and the second interface area between the electrode and a lumen wall at the treatment location increasing during the third deployment phase, and
  a fourth deployment phase following the third deployment phase, the third interface area is more stable than it is during the third deployment phase; and
using the electrode to measure an electrical property of a sum of material adjacent to the electrode while deploying the neuromodulation element, the sum of material adjacent to the electrode including portions of the dielectric sleeve, the lumen wall and the biological fluid adjacent to the electrode;
detecting a transition of the electrical property corresponding to a transition from the third deployment phase to the fourth deployment phase; and
generating a status indication, enabling a neuromodulation treatment, or both in response to detecting the transition of the electrical property.

22. The method of example 21 wherein the electrical property is impedance.

23. The method of example 21 or example 22 wherein detecting the transition of the electrical property includes detecting a transition of a rate of change of the electrical property.

24. The method of example 21 or example 22 wherein detecting the transition of the electrical property includes:
detecting a rate of change of the electrical property to be greater than a first threshold rate of change for a first time period; and
detecting the rate of change of the electrical property to be less than a second threshold rate of change for a second time period after the first time period.

25. The method of any of examples 21-24 wherein the electrode is a wire electrode.

26. The method of example 25 wherein the wire electrode is at least generally helical during the fourth deployment phase.

27. The method of any of examples 21-26 wherein deploying the neuromodulation element includes pushing a proximal end of the electrode in a distal direction.

VI. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Certain aspects of the present technology may take the form of computer-executable instructions, including routines executed by a controller or other data processor. In some embodiments, a controller or other data processor is specifically programmed, configured, and/or constructed to perform one or more of these computer-executable instructions. Furthermore, some aspects of the present technology may take the form of data (e.g., non-transitory data) stored or distributed on computer-readable media, including magnetic or optically readable and/or removable computer discs as well as media distributed electronically over networks. Accordingly, data structures and transmissions of data particular to aspects of the present technology are encompassed within the scope of the present technology. The present technology also encompasses methods of both programming computer-readable media to perform particular steps and executing the steps.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method for neuromodulation energy delivery, comprising:
determining a longitudinal shift of a neuromodulation element of a catheter relative to an elongate shaft of the catheter during deployment of the catheter in a body lumen of a patient, wherein the elongate shaft is coupled to the neuromodulation element and configured to be delivered to a treatment location within the body lumen; and
determining an inner diameter of the body lumen at the treatment location based on the longitudinal shift.

2. The method of claim 1, further comprising:
correlating values of the longitudinal shift to values of the inner diameter of the inner diameter of the body lumen based on predetermined data, wherein determining the inner diameter of the body lumen is based on the correlation.

3. The method of claim 1, further comprising:
controlling or adjusting energy delivery based on the inner diameter of the body lumen.

4. The method of claim 3, wherein an amount of energy that is delivered has a direct or indirect linear relationship with the longitudinal shift of the neuromodulation element at a time of detection of stable contact.

5. The method of claim 4, wherein the amount of energy that is delivered increases as the longitudinal shift of the neuromodulation element is greater and the amount of energy that is delivered decreases as the longitudinal shift of the neuromodulation element is less.

6. The method of claim 3, wherein an amount of time that the energy is delivered increases as the longitudinal shift of the neuromodulation element is greater and the amount of time that the energy is delivered decreases as the longitudinal shift of the neuromodulation element is less.

7. The method of claim 1, further comprising:
   detecting or determining that the neuromodulation element is in stable contact with a wall of the body lumen of the patient.

8. The method of claim 7, wherein detecting or determining that the neuromodulation element is in stable contact with the wall of the body lumen of the patient is based on measured impedance values.

9. An apparatus for neuromodulation treatment, comprising:
   a catheter comprising an elongate shaft that is configured to be delivered to a treatment site within a body lumen of a patient;
   a neuromodulation element coupled to the elongate shaft and configured to be positioned into contact with and deliver energy to a wall of the body lumen; and
   a console coupled to the neuromodulation element and configured to:
      determine a longitudinal shift of the neuromodulation element;
      determine an inner diameter of the vessel at the treatment site based on the longitudinal shift, and
      deliver neuromodulation energy to the treatment site within the body lumen based on the inner diameter of the body lumen.

10. The apparatus of claim 9, wherein the console is configured to:
    determine that the neuromodulation element is in stable contact with the wall of the body lumen based on measured impedance values.

11. The apparatus of claim 10, wherein to deliver the neuromodulation energy to the treatment site the console is configured to:
    deliver an amount of energy that has a direct or indirect linear relationship with the longitudinal shift of the neuromodulation element at a time of detection of stable contact with the body lumen.

12. The apparatus of claim 11, wherein the console is configured such that the amount of energy that is delivered increases as the longitudinal shift of the neuromodulation element is greater and the amount of energy that is delivered decreases as the longitudinal shift of the neuromodulation element is less.

13. The apparatus of claim 9, wherein the console is configured such that an amount of time that the energy is delivered increases as the longitudinal shift of the neuromodulation element is greater and the amount of time that the energy is delivered decreases as the longitudinal shift of the neuromodulation element is less.

14. The apparatus of claim 9, further comprising:
    a gauge coupled to the neuromodulation element and configured to measure the longitudinal shift of the neuromodulation element relative to the elongate shaft during deployment of the catheter in the body lumen.

15. The apparatus of claim 14, wherein the console is configured to correlate values of the longitudinal shift to values of the inner diameter of the inner diameter of the body lumen based on predetermined data.

16. The apparatus of claim 15, wherein the console is configured to determine the inner diameter of the body lumen based on the correlation.

17. An apparatus for neuromodulation treatment, the apparatus comprising:
    a catheter comprising an elongate shaft that is configured to be delivered to a treatment site within a body lumen of a patient;
    an electrode coupled to the elongate shaft and configured to be positioned into contact with and deliver energy to a wall of the body lumen; and
    a console coupled to the electrode and configured to:
       determine the longitudinal shift of the electrode;
       determine an inner diameter of the body lumen at the treatment site based on the longitudinal shift, and
       deliver neuromodulation energy to the treatment site within the body lumen based on the inner diameter of the body lumen.

18. The apparatus of claim 17, further comprising:
    a gauge coupled to the electrode and configured to measure a longitudinal shift of the electrode relative to the elongate shaft during deployment of the catheter in the body lumen.

19. The apparatus of claim 17, wherein the console is configured to determine the inner diameter of the body lumen further based on a correlation of values of the longitudinal shift to values of the inner diameter.

20. The apparatus of claim 17, wherein the console is configured such that an amount of energy that is delivered increases as the longitudinal shift of the electrode is greater and the amount of energy that is delivered decreases as the longitudinal shift of the electrode is less.

* * * * *